United States Patent
Murphy et al.

(10) Patent No.: US 10,238,767 B2
(45) Date of Patent: Mar. 26, 2019

(54) MONO-LAYER THIN FILM ADHESIVE COMPOUNDS AND METHODS OF SYNTHESIS AND USE

(71) Applicant: DSM IP ASSETS B.V., TE HEERLEN (NL)

(72) Inventors: John L. Murphy, Madison, WI (US); Jeffrey L. Dalsin, Verona, WI (US); Arinne N. Lyman, Neenah, WI (US); Laura L. Bremer, Lodi, WI (US); Joel L. Broussard, Madison, WI (US); Neil Winterbottom, San Mateo, CA (US); Justin T. Koepsel, Madison, WI (US)

(73) Assignee: DSM IP ASSETS, B.V., Heerlen (NL)

( * ) Notice: Subject to any disclaimer, the term of this patent is extended or adjusted under 35 U.S.C. 154(b) by 779 days.

(21) Appl. No.: 13/951,182

(22) Filed: Jul. 25, 2013

(65) Prior Publication Data
US 2014/0030944 A1   Jan. 30, 2014

Related U.S. Application Data

(60) Provisional application No. 61/675,559, filed on Jul. 25, 2012.

(51) Int. Cl.
*A61L 24/00* (2006.01)
*A61L 24/04* (2006.01)
(Continued)

(52) U.S. Cl.
CPC .......... *A61L 24/046* (2013.01); *A61L 24/001* (2013.01); *A61L 27/34* (2013.01); *A61L 27/50* (2013.01); *A61L 31/10* (2013.01); *A61L 31/14* (2013.01); *C08G 63/664* (2013.01); *C08G 63/6852* (2013.01); *C08G 69/40* (2013.01); *C08G 69/44* (2013.01); *C09D 177/12* (2013.01); *C09J 177/12* (2013.01); *A61L 24/00* (2013.01); *A61L 24/04* (2013.01); *B32B 7/12* (2013.01); *B32B 27/08* (2013.01); *B32B 27/12* (2013.01); *B32B 27/18* (2013.01); *B32B 27/26* (2013.01); *B32B 27/28* (2013.01); *B32B 27/285* (2013.01); *B32B 27/34* (2013.01); *B32B 27/36* (2013.01);
(Continued)

(58) Field of Classification Search
None
See application file for complete search history.

(56) References Cited

U.S. PATENT DOCUMENTS 7,622,533 B2 *  11/2009  Lee ................. C08G 65/33389
                                              525/328.2
7,858,679 B2 *  12/2010  Messersmith .......... A61L 31/06
                                              424/1.69
(Continued)

FOREIGN PATENT DOCUMENTS

WO    WO 2010/091298    *  8/2010

OTHER PUBLICATIONS

Wee, Andrew et al. "Tetraethylammonium Periodate" (http://reag.paperplane.io/00002617.htm) (Year: 2000).*
(Continued)

*Primary Examiner* — Vivian Chen
(74) *Attorney, Agent, or Firm* — Kevin M. Bull

(57) ABSTRACT

The invention relates provides synthetic medical adhesives which exploit plant derivatives to form covalent bonds with amines and thiols on tissue surfaces.

29 Claims, 23 Drawing Sheets

(51) Int. Cl.
*C08K 5/04* (2006.01)
*C08K 5/17* (2006.01)
*C08K 5/19* (2006.01)
*B32B 7/12* (2006.01)
*B32B 27/08* (2006.01)
*B32B 27/12* (2006.01)
*B32B 27/18* (2006.01)
*B32B 27/26* (2006.01)
*B32B 27/28* (2006.01)
*B32B 27/34* (2006.01)
*B32B 27/36* (2006.01)
*B32B 27/40* (2006.01)
*C08L 67/00* (2006.01)
*C08L 67/04* (2006.01)
*C08L 69/00* (2006.01)
*C08L 71/00* (2006.01)
*C08L 75/02* (2006.01)
*C08L 75/04* (2006.01)
*C08L 77/00* (2006.01)
*C08L 77/12* (2006.01)
*C08L 79/02* (2006.01)
*C09D 167/00* (2006.01)
*C09D 167/04* (2006.01)
*C09D 169/00* (2006.01)
*C09D 171/00* (2006.01)
*C09D 175/02* (2006.01)
*C09D 175/04* (2006.01)
*C09D 177/00* (2006.01)
*C09D 177/12* (2006.01)
*C09D 179/02* (2006.01)
*C09J 5/02* (2006.01)
*C09J 11/06* (2006.01)
*C09J 167/00* (2006.01)
*C09J 167/04* (2006.01)
*C09J 169/00* (2006.01)
*C09J 171/00* (2006.01)
*C09J 175/02* (2006.01)
*C09J 175/04* (2006.01)
*C09J 177/00* (2006.01)
*C09J 177/12* (2006.01)
*C09J 179/02* (2006.01)
*C08G 63/00* (2006.01)
*C08G 63/06* (2006.01)
*C08G 63/08* (2006.01)
*C08G 63/66* (2006.01)
*C08G 63/68* (2006.01)
*C08G 63/685* (2006.01)
*C08G 63/664* (2006.01)
*C08G 63/91* (2006.01)
*C08G 64/00* (2006.01)
*C08G 69/00* (2006.01)
*C08G 69/40* (2006.01)
*C08G 69/44* (2006.01)
*C08G 69/48* (2006.01)
*C08G 71/00* (2006.01)
*C08G 73/02* (2006.01)
*C08G 65/00* (2006.01)
*A61L 27/34* (2006.01)
*A61L 27/50* (2006.01)
*A61L 31/10* (2006.01)
*A61L 31/14* (2006.01)

(52) U.S. Cl.
CPC ........... *B32B 27/40* (2013.01); *B32B 2250/02* (2013.01); *B32B 2250/03* (2013.01); *B32B 2255/02* (2013.01); *B32B 2255/26* (2013.01); *B32B 2255/28* (2013.01); *B32B 2405/00* (2013.01); *B32B 2535/00* (2013.01); *C08G 63/00* (2013.01); *C08G 63/06* (2013.01); *C08G 63/08* (2013.01); *C08G 63/66* (2013.01); *C08G 63/68* (2013.01); *C08G 63/685* (2013.01); *C08G 63/91* (2013.01); *C08G 63/912* (2013.01); *C08G 64/00* (2013.01); *C08G 65/00* (2013.01); *C08G 69/00* (2013.01); *C08G 69/48* (2013.01); *C08G 71/00* (2013.01); *C08G 73/02* (2013.01); *C08G 73/024* (2013.01); *C08K 5/04* (2013.01); *C08K 5/17* (2013.01); *C08K 5/19* (2013.01); *C08L 67/00* (2013.01); *C08L 67/04* (2013.01); *C08L 69/00* (2013.01); *C08L 71/00* (2013.01); *C08L 75/02* (2013.01); *C08L 75/04* (2013.01); *C08L 77/00* (2013.01); *C08L 77/12* (2013.01); *C08L 79/02* (2013.01); *C09D 167/00* (2013.01); *C09D 167/04* (2013.01); *C09D 169/00* (2013.01); *C09D 171/00* (2013.01); *C09D 175/02* (2013.01); *C09D 175/04* (2013.01); *C09D 177/00* (2013.01); *C09D 179/02* (2013.01); *C09J 5/02* (2013.01); *C09J 11/06* (2013.01); *C09J 167/00* (2013.01); *C09J 167/04* (2013.01); *C09J 169/00* (2013.01); *C09J 171/00* (2013.01); *C09J 175/02* (2013.01); *C09J 175/04* (2013.01); *C09J 177/00* (2013.01); *C09J 179/02* (2013.01); *C09J 2203/00* (2013.01); *Y10T 428/2848* (2015.01); *Y10T 428/2852* (2015.01); *Y10T 428/31536* (2015.04); *Y10T 428/31551* (2015.04); *Y10T 428/31558* (2015.04); *Y10T 428/31725* (2015.04); *Y10T 428/31786* (2015.04); *Y10T 428/31794* (2015.04); *Y10T 442/10* (2015.04); *Y10T 442/2738* (2015.04)

(56) References Cited

U.S. PATENT DOCUMENTS

| | | | | |
|---|---|---|---|---|
| 8,383,092 B2 * | 2/2013 | Lee | ........................ | A61L 24/001 424/78.08 |
| 8,563,117 B2 * | 10/2013 | Messersmith | .............. | C08J 7/12 156/249 |
| 8,673,286 B2 * | 3/2014 | Messersmith | ....... | C08G 65/3317 424/78.02 |
| 8,745,285 B2 * | 6/2014 | Eguchi | ............. | H04N 21/43637 710/15 |
| 8,815,793 B2 * | 8/2014 | Messersmith | .......... | A61L 24/046 514/1.1 |
| 8,916,652 B2 * | 12/2014 | Dalsin | ..................... | A61L 29/16 525/408 |
| 9,115,289 B2 * | 8/2015 | Lee | ........................ | A61L 15/18 |
| 9,320,826 B2 * | 4/2016 | Lee | ..................... | A61L 24/046 |
| 9,670,386 B2 * | 6/2017 | Reyes | ................... | C09J 101/08 |
| 2003/0199017 A1 * | 10/2003 | Reymond | ............ | C07D 311/16 435/25 |
| 2005/0014212 A1 * | 1/2005 | Reymond | ................ | C12Q 1/26 435/15 |
| 2008/0171836 A1 * | 7/2008 | Lee | .................. | C08G 65/33389 525/418 |
| 2008/0247984 A1 * | 10/2008 | Messersmith | ....... | C08G 65/3317 424/78.02 |
| 2010/0113828 A1 * | 5/2010 | Dalsin | .................... | A01N 37/38 564/153 |
| 2010/0137902 A1 * | 6/2010 | Lee | ....................... | A61L 24/001 606/213 |
| 2010/0137903 A1 * | 6/2010 | Lee | ..................... | A61K 31/765 606/213 |

(56) References Cited

U.S. PATENT DOCUMENTS

| | | | |
|---|---|---|---|
| 2012/0016390 A1* | 1/2012 | Lee .................. | A61L 31/10 |
| | | | 606/151 |
| 2012/0029559 A1* | 2/2012 | Lee .................. | A61L 15/18 |
| | | | 606/214 |
| 2012/0116424 A1* | 5/2012 | Lee .................. | A61L 24/046 |
| | | | 606/151 |
| 2012/0179083 A1* | 7/2012 | Lee .................. | A61K 31/74 |
| | | | 602/52 |
| 2017/0056548 A1* | 3/2017 | Lee .................. | A61L 24/046 |
| 2017/0266353 A1* | 9/2017 | Murphy ............ | A61L 31/10 |

OTHER PUBLICATIONS

Miao, H et al., "Fluorinated modification of hyperbranched polyesters used for improving the surface property of UV curing coatings" Journal of Fluorine Chemistry, vol. 131, No. 12, pp. 1356-1361, Oct. 29, 2010.

Nizamov, IS et al. "Phosphorus-containing Hyperbranched Structures. Phosphorylation of Hyperbranched Polyols with 2-(Diethylamino)-1,2,3-dioxaphosphinane" Russian Journal of General Chemistry, vol. 78, No. 7, pp. 1338-1340, 2008.

* cited by examiner

| Compound | Volumetric Swelling Rato (%)@ 37°C | Degradation @ 55°C (Accelerated) | Degradation @ 37°C (Real-Time) |
|---|---|---|---|
| Medhesive-181 | 23.88+/-102.82% | 6.33+/-0.58 days | 93.67+/-13.80 days |
| Medhesive-145 | 29.50+/-13.97% | 14.33+/-0.58 days | 167+/-3.46 days |
| Medhesive-179 | 36.38+/-87.50% | 18.33+/-0.58 days | 240.33+/-30.60 days |

| Entry | Medhesive | moles oxidant : moles PD | Mean Lap shear strength (KPa) |
|---|---|---|---|
| 1 | 145 | 1.5:1 | 33.3 |
| 2 | 179 | 1.5:1 | 35.3 |
| 3 | 188 | 1.5:1 | 28.0 |
| 4 | 194 | 1.5:1 | 5.0 |
| 5 | 202 | 1.5:1 | 59.7 |

MONO-LAYER THIN FILM ADHESIVE COMPOUNDS AND METHODS OF SYNTHESIS AND USE

CROSS-REFERENCE TO RELATED APPLICATION

The present application claims priority to U.S. Provisional Application 61/675,559, filed Jul. 25, 2012, which is herein incorporated by reference in its entirety.

REFERENCE TO FEDERAL FUNDING

This project was funded in part by NIH (2R44AR056519-02 and 1R43GM096527-01). NMR characterization was performed at NMRFAM, which is supported by NIH (2R44AR056519-02 and 1R43GM096527-01) grants. The government has certain rights in the invention.

FIELD OF THE INVENTION

The invention relates generally to new synthetic medical adhesives which exploit key plant derivatives to form covalent bonds with amines and thiols on tissue surfaces. These plant derivatives are capable of undergoing oxidative processes to form these bonds with the tissue surface as well as themselves. Specifically, these phenolic derivatives are capable of being attached to polymeric units. These polymeric units can then be conformed to a thin film with an oxidant placed directly within the film. Upon hydration, the film activates to form crosslinks with the amines and thiols on the tissue surface (adhesive) as well as other phenolics (cohesive).

BACKGROUND OF THE INVENTION

Phenolic derivatives, such as catechol, guaiacol and syringol derivatives are naturally occurring compounds found in nature. Catechol moieties are often associated with mussel adhesive proteins (MAPs) which utilize this derivative to form tenacious bonds in aqueous solutions. Alternatively, guaiacol and syringol derivatives are often associated with plants, and form the structural components of lignins. These structural components are formed through the oxidative crosslinking of the phenolic group to form polymeric structures. It was found this oxidative process also forms covalent bonds between amines and thiols on tissue surfaces. As such, specific phenolics which allow for the incorporation of oxidants may be used as medical adhesives. The medical adhesives may be constructed into a thin film in which oxidant is incorporated directly into the polymer film allowing for strong interfacial binding to a support and tissue when hydrated.

Ferulic acid, sinapic acid and syringic acid adhesive endgroups are found naturally in plants, typically as structural components through an oxidative polymerization reaction to form lignins. Generally, the adhesive endgroups comprise a double bond between the phenolic ring and carboxylic acid. They contain at least 1 methoxy group (ferulic acid) and no more than two methoxy groups (sinapic acid and syringic acid). Methoxy groups may be preferable at the 3 position, or at both the 3 and 5-position. They also may contain at least one hydroxyl group, typically at the 4-position of the aromatic ring, and the methoxy group(s) are next to this hydroxyl group (3, or 3 and 5 position) such that hydroxyl group(s) may be switched with the methoxy group as, for example, in Medhesive-188, i.e., with isoferulic acid, wherein the hydroxyl group is at the 3-position while the methoxy group is at the 4 position. Accordingly, a hydroxyl group may be placed around the aromatic ring as well as up to two methoxy groups. Additionally, ferulic acid and sinapic acid may contain a double bond between the phenolic aromatic ring and the carboxylic acid. Compounds with carboxylic acids attached directly to the phenolic ring (e.g., benzoic acid derivatives) such as Medhesive 194 (i.e., syringic acid) may also be adhesive, even though they lack the double bond between the phenolic ring and carboxylic acid.

In medical practice, few adhesives exist which provide both robust adhesion in a wet environment and suitable mechanical properties to be used as a tissue adhesive or sealant. For example, fibrin-based tissue sealants (e.g. Tisseel VH, Baxter Healthcare) provide a mechanical match for natural tissue, but possess poor tissue-adhesion characteristics. Conversely, cyanoacrylate adhesives (e.g. Dermabond, Ethicon, Inc.) produce adhesive bonds with surfaces, but may be stiff and brittle with regard to mechanical properties and release formaldehyde as they degrade.

Therefore, a need exists for materials that overcome one or more of the current disadvantages.

BRIEF SUMMARY OF THE INVENTION

The present invention surprisingly provides multi-armed phenyl derivatives (PDs) comprising, for example, guaiacol derivatives (PDs) having the general formula (I) which can be compounded with an oxidant:

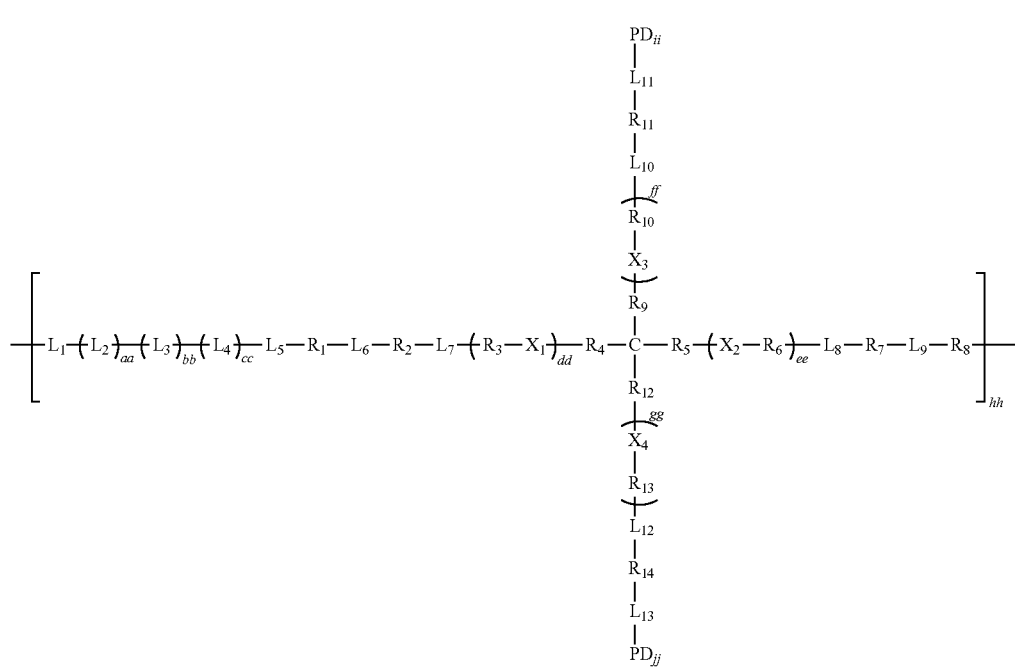

(I)

wherein each $L_2$, $L_3$ and $L_4$ independently, is a linker;

each $L_1$, $L_5$, $L_6$, $L_7$, $L_8$, $L_9$, $L_{10}$, $L_{11}$ $L_{12}$ and $L_{13}$ independently, is a linker or a suitable linking group selected from amine, amide, ether, ester, urea carbonate or urethane linking groups;

each $X_1$, $X_2$, $X_3$ and $X_4$ independently, is an oxygen atom or NR;

$R_1$ if present, is H or a branched or unbranched C1-C10 alkyl group;

each $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ independently, is a branched or unbranched C1-C15 alkyl group;

each $PD_{ii}$ and $PD_{jj}$, independently, is a phenyl derivative residue;

aa is a value from 0 to about 80;
bb is a value from 0 to about 80;
cc is a value from 0 to about 80;
dd is a value from 1 to about 120;
ee is a value from 1 to about 120;
ff is a value from 1 to about 120;
gg is a value from 1 to about 120; and
hh is a value from 1 to about 80.

In one embodiment, the compound of formula (I) $L_1$ is a residue of succinic acid; $L_2$ is a residue of a polycaprolactone or polylactic acid (thus forming an ester bond between terminal ends of the succinic acid and the hydroxyl oxygen of the ring opened lactone); $L_3$ is a residue of diethylene glycol (thus forming an ester bond between the ester portion of the lactone and one terminal hydroxyl group of the glycol); $L_4$ is a residue of a polycaprolactone or a polylactic acid (therefore forming an ester linkage between a second terminal end of a hydroxyl group of the glycol and the ring opened caprolactone); $L_5$ is a residue of succinic acid or anhydride; $L_7$, $L_8$, $L_{10}$, and $L_{12}$ represent an ester linkage from the terminal hydroxyl group on the terminal end of a hydroxyl terminated polyethylene glycol polyether to $R_2$, $R_7$, $R_{11}$, and $R_{14}$, respectively; $R_2$, $R_7$, $R_{11}$, and $R_{14}$ are branched or unbranched alkane chains ranging from C1-C15; $R_3$, $R_6$, $R_{10}$ and $R_{13}$ are each —$CH_2CH_2$—; $X_1$, $X_2$, $X_3$ and $X_4$ are each O; $R_4$, $R_5$, $R_9$ and $R_{12}$ are each —$CH_2$—; $L_{11}$ and $L_{13}$ form an amide linkage between the terminal end of the PD and the respective R; and $PD_{ii}$ and $PD_{jj}$ are ferulic acid (FA) residues.

In further embodiments, FIGS. 1-8 and 10-15 provide compounds that depict certain aspects of the invention.

Compounds 1, 7, and 8, for example, have a Wt % FA (Ferulic Acid) typically between 2.8-3.2 Wt % by UV-VIS, a PCL Wt % typically 17.5-18.5 Wt % by $^1$H NMR in DMSO and a PEG Wt % typically between 78.5 and 80.5 Wt % by $^1$H NMR in DMSO. Compound I typically has DSC values between 39-42° C. for the second heating cycle and a typical intrinsic viscosity value between 0.75-1.5 dl/g.

In one embodiment, the reaction products of the syntheses described herein are included as compounds or compositions useful as adhesives or surface treatment/anti-fouling aids. It should be understood that the reaction product(s) of the synthetic reactions may be purified by methods, such as diafiltration, chromatography, recrystallization/precipitation and the like or can be used without further purification.

In still further embodiments blends of the compounds of the invention described herein, may be prepared with various polymers. Polymers suitable for blending with the compounds of the invention are selected to impart non-covalent interactions with the compound(s), such as hydrophobic-hydrophobic interactions or hydrogen bonding with an oxygen atom on PEG and a substrate surface. These interactions may increase the cohesive properties of the film to a substrate. If a biopolymer is used, it may introduce specific bioactivity to the film, (i.e. biocompatibility, cell binding, immunogenicity, etc.).

Generally, there are four classes of polymers useful as blending agents with the compounds of the invention. Class 1 includes: Hydrophobic polymers (polyesters, PPG) with terminal functional groups (—OH, COOH, etc.), linear PCL-diols (MW 600-2000), branched PCL-triols (MW 900), wherein PCL can be replaced with PLA, PGA, PLAGA, and other polyesters.

Class 2 includes amphiphilic block (di, tri, or multiblock) copolymers of PEG and polyester or PPG, tri-block copolymers of PCL-PEG-PCL (PCL MW=500-3000, PEG MW=500-3000), tri-block copolymers of PLA-PEG-PLA (PCL MW=500-3000, PEG MW=500-3000). In other embodiments, PCL and PLA can be replaced with PGA, PLGA, and other polyesters. Pluronic polymers (triblock, diblock of various MW) and other PEG, PPG block copolymers are also suitable.

Class 3 includes hydrophilic polymers with multiple functional groups (—OH, —NH2, —COOH) along the polymeric backbone. These include, for example, PVA (MW 10,000-100,000), poly acrylates and poly methacrylates, and polyethylene imines.

Class 4 includes biopolymers such as polysaccharides, hyaluronic acid, chitosan, cellulose, or proteins, etc. which contain functional groups.

Abbreviations: PCL=polycaprolactone, PLA=polylactic acid, PGA=Polyglycolic acid, PLGA=a random copolymer of lactic and glycolic acid, PPG=polypropyl glycol, and PVA=polyvinyl alcohol.

It should be understood that the compounds of the invention may be coated multiple times to form bi, tri, etc. layers. The layers may be of the compounds of the invention per se, or of blends of a compound(s) and polymer, or combinations of a compound layer and a blend layer, etc.

Consequently, constructs may also include such layering of the compounds per se, blends thereof, and/or combinations of layers of a compound(s) per se and a blend or blends.

The adhesives of the invention described throughout the specification may be utilized for wound closure and materials of this type are often referred to as tissue sealants or surgical adhesives.

The compounds of the invention may be applied to a suitable substrate surface as a film or coating. Application of the compound(s) to the surface inhibits or reduces the growth of biofilm (bacteria) on the surface relative to an untreated substrate surface. In other embodiments, the compounds of the invention may be employed as an adhesive.

Exemplary applications include, but are not limited to fixation of synthetic (resorbable and non-resorbable) and biological membranes and meshes for hernia repair, void-eliminating adhesive for reduction of post-surgical seroma formation in general and cosmetic surgeries, fixation of synthetic (resorbable and non-resorbable) and biological membranes and meshes for tendon and ligament repair, sealing incisions after ophthalmic surgery, sealing of venous catheter access sites, bacterial barrier for percutaneous devices, as a contraceptive device, a bacterial barrier and/or drug depot for oral surgeries (e.g. tooth extraction, tonsillectomy, cleft palate, etc.), for articular cartilage repair, for antifouling or anti-bacterial adhesion.

BRIEF DESCRIPTION OF THE DRAWINGS

FIG. 9: Shows a degradation profile of Medhesive-145, 179, 181 coated onto a polyester mesh. Samples tested were at coating densities of 250 g/m$^2$ obtained by heat pressing two 125 g/m$^2$ films into a synthetic mesh. The mesh type they were coated onto was a polyester mesh with a coating density of 30 g/m$^2$. The oxidant used was sodium periodate. The amount of $IO_4^-$:FA was 1.5:1. For testing, a film 25 mm×80 mm in area was activated with 555 uL of 1×PBS on both sides for 20 minutes under a glass slide and release liner. A 10 mm hole punch was used to cut out pieces (14). 8 samples were used to collect swelling data. 3 samples were used for a 37° C. pilot degradation study and 3 were used for a 55° C. pilot degradation study. All samples were placed into 15 mL of 1×PBS buffer for testing.

FIG. 23: Representative lap shear data for Medhesive polymers shown in Table 1. Comparison between Entries 1 and 2 reveal that the nature of the linking group alone does not strongly impact lap shear strength. The nature of the phenyl derivative (PD) group, however, can influence the overall lap shear strength as shown when Entries 4 and 5 are compared with Entry 2, where the PD group in Entries 4 and 5 are based on isoferulic acid and syringic acid respectively. Comparison between Entry 5 and Entry 2 shows that the nature of polyester residue can also impact the lap shear strength, such that incorporation of a polylactic acid polymer residue results in a polymer film with higher strength. Since all samples exhibited adhesive failure when tested, i.e. breaking occurred between the polymer film and tissue sample, adhesive strength can be tailored by varying molecular structure of the constituent parts of the polymer.

DETAILED DESCRIPTION

Figure 1:
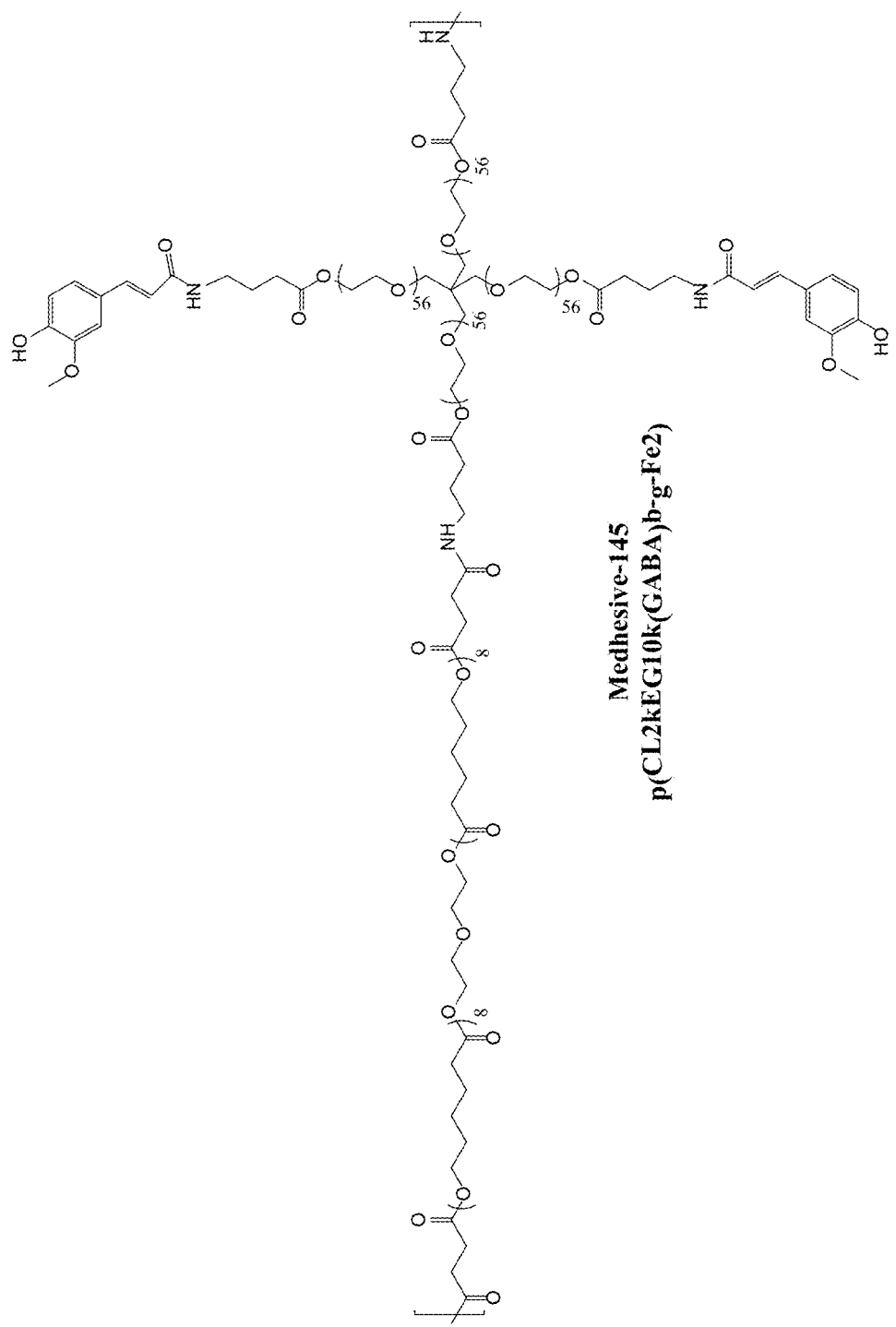
FIG. 1: Depicts general structure of Medhesive-145.
Figure 2:
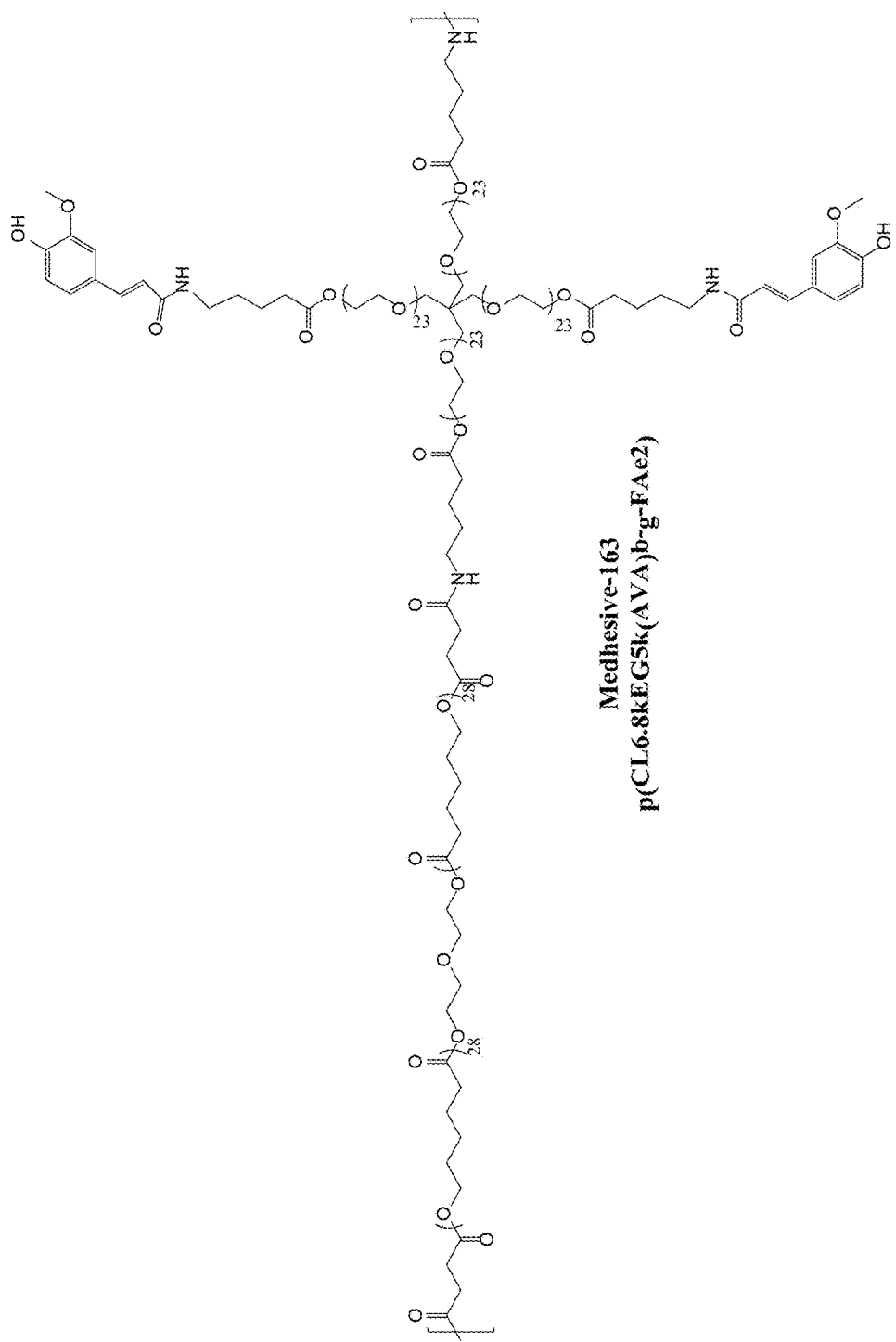
FIG. 2: Depicts general structure of Medhesive-163.
Figure 3:
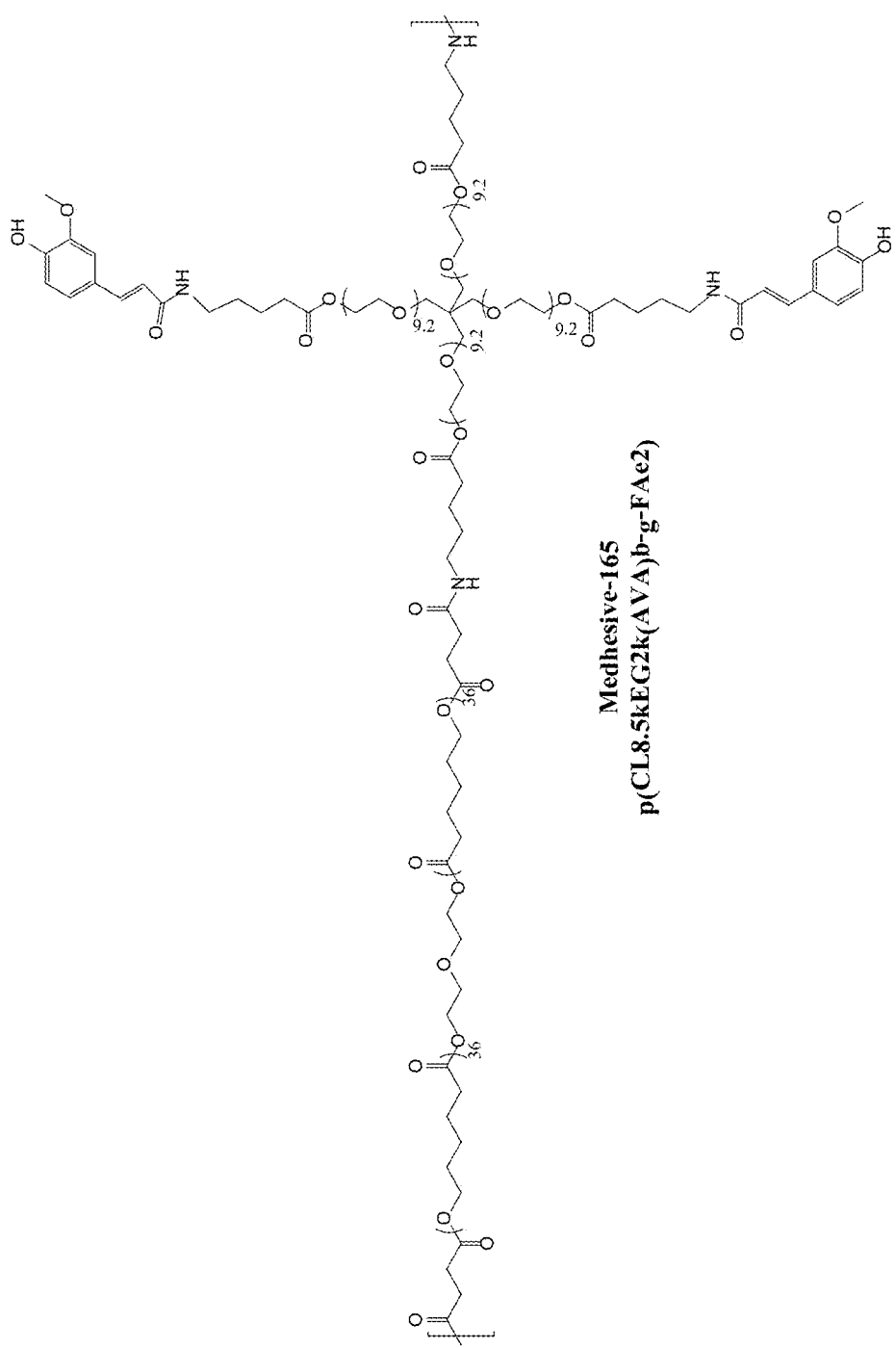
FIG. 3: Depicts general structure of Medhesive-165
Figure 4:
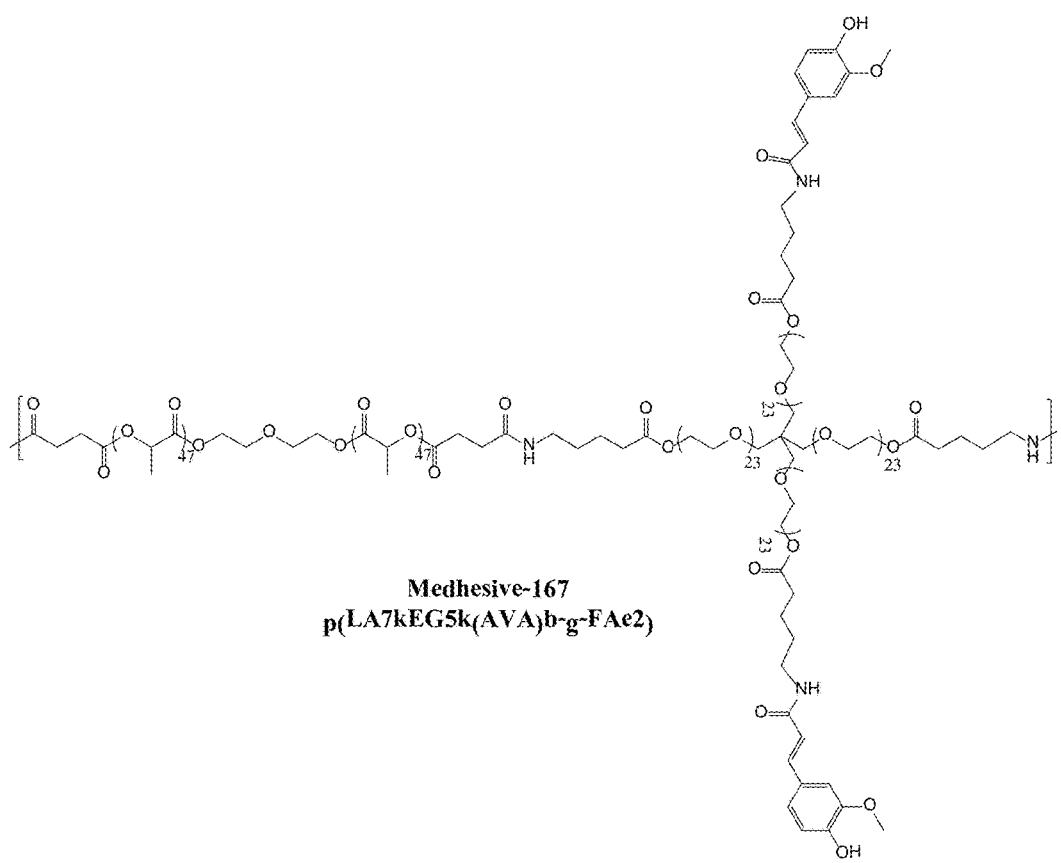
FIG. 4: Depicts general structure of Medhesive-167.
Figure 5:
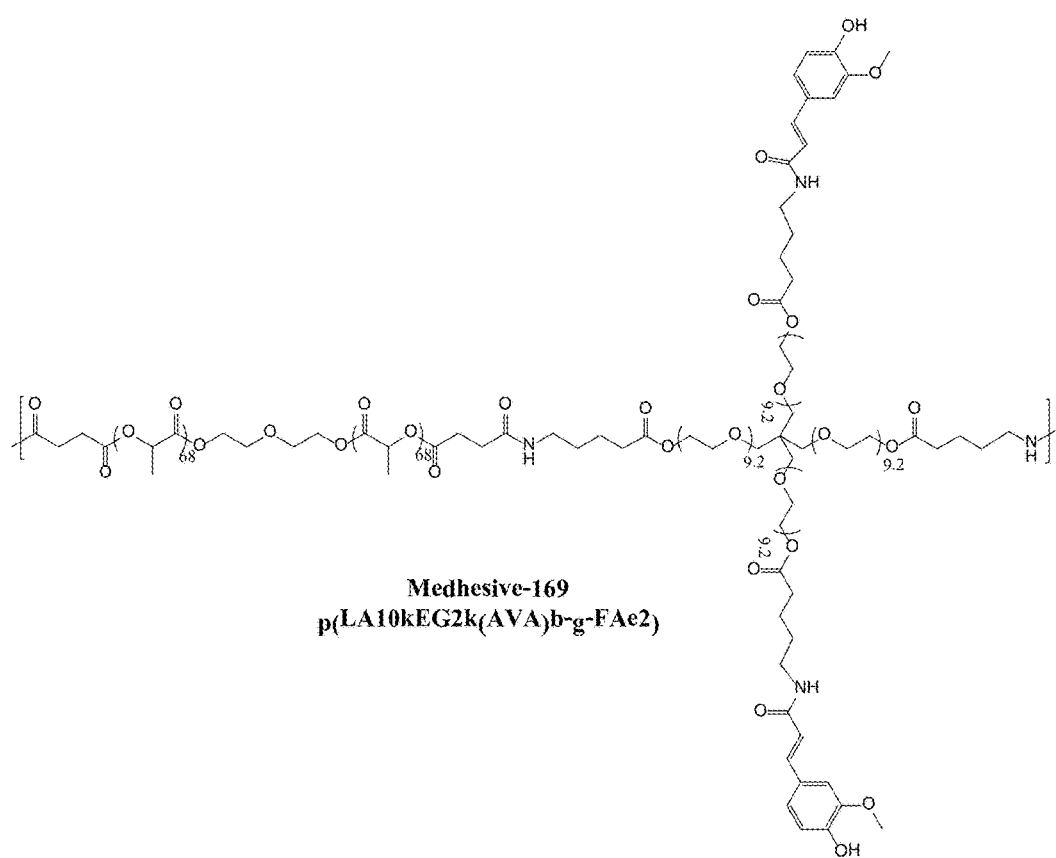
FIG. 5: Depicts general structure of Medhesive-169.
Figure 6:
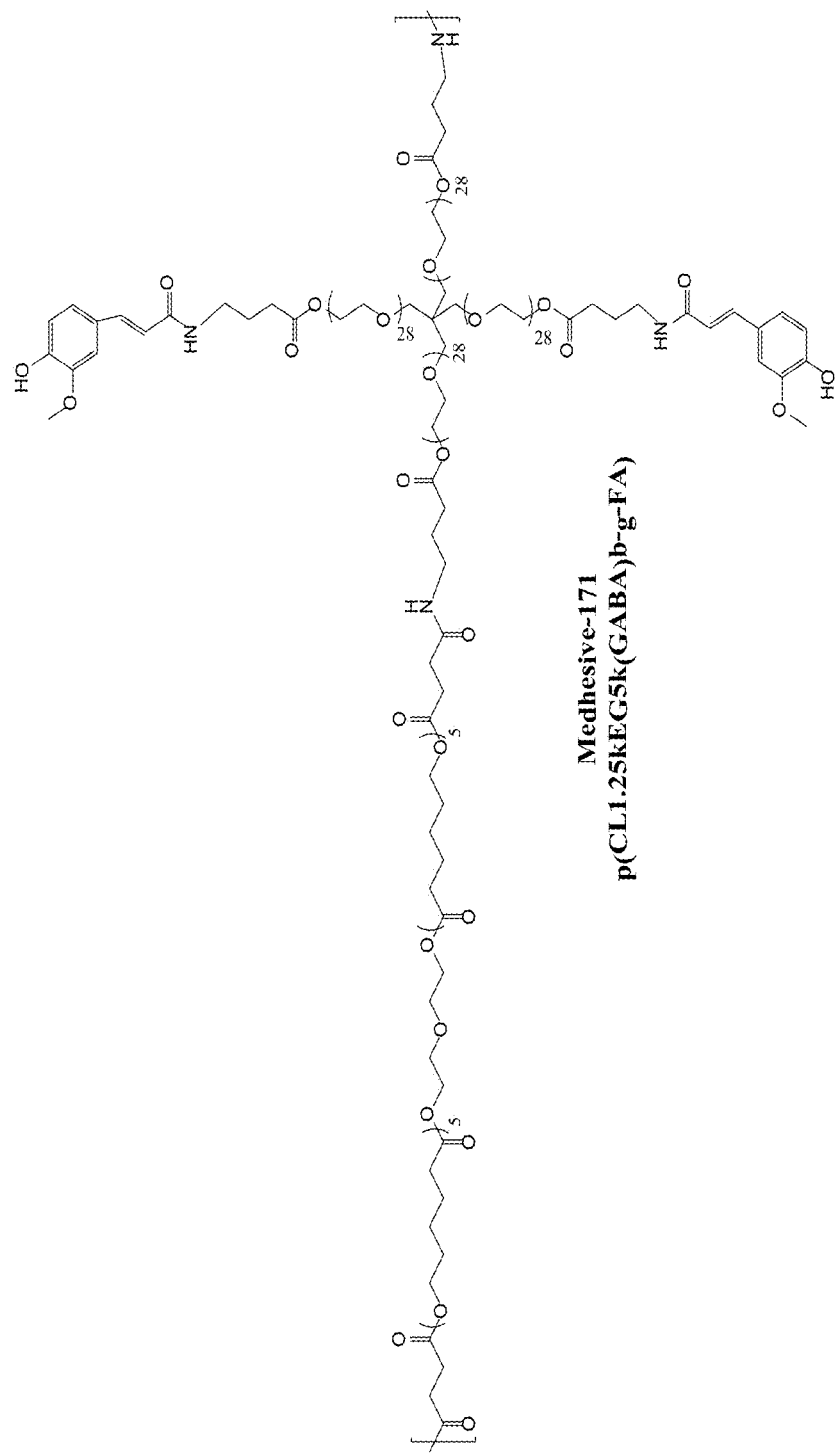
FIG. 6: Depicts general structure of Medhesive-171.
Figure 7:
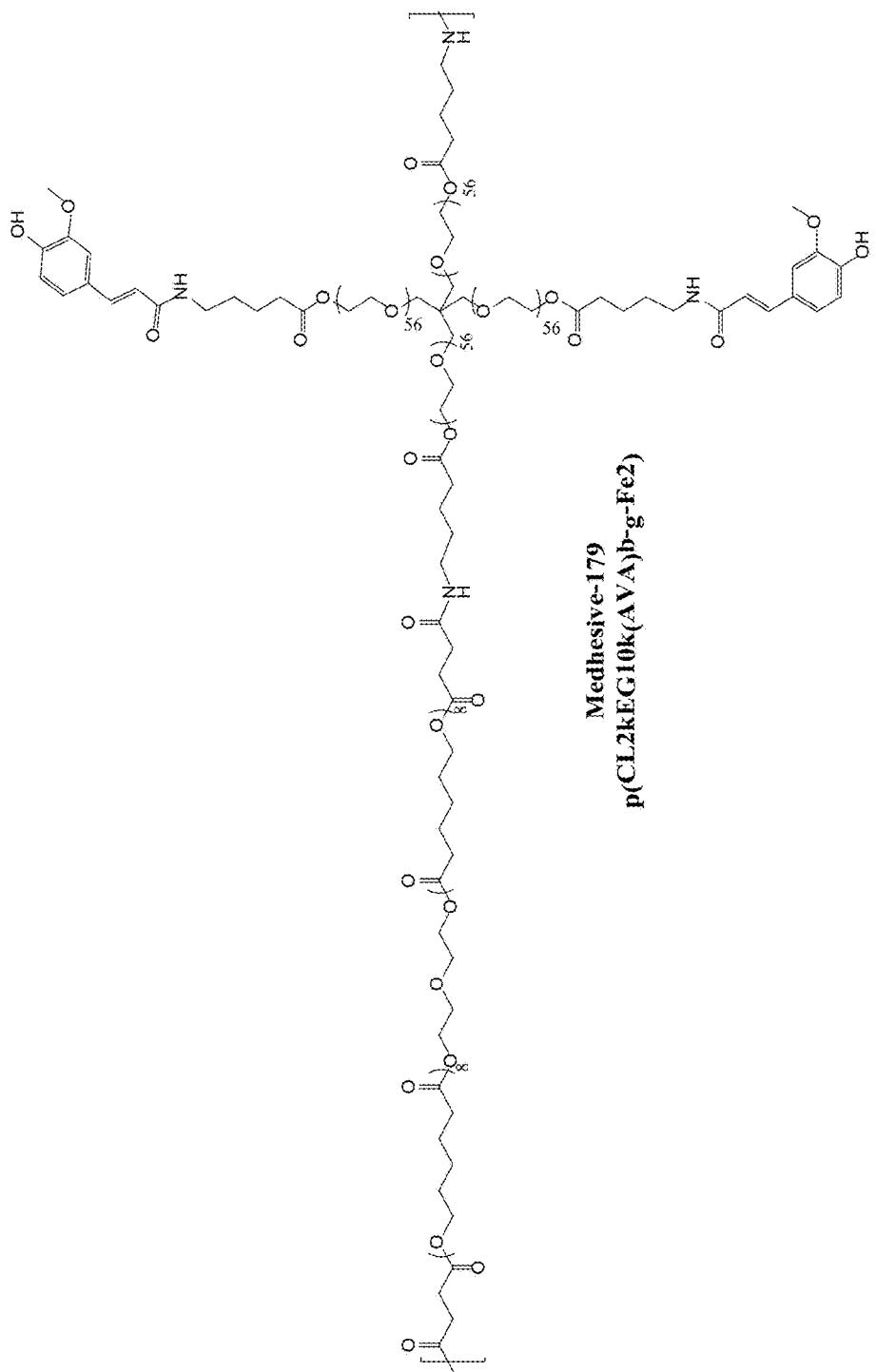
FIG. 7: Depicts general structure of Medhesive-179.
Figure 8:
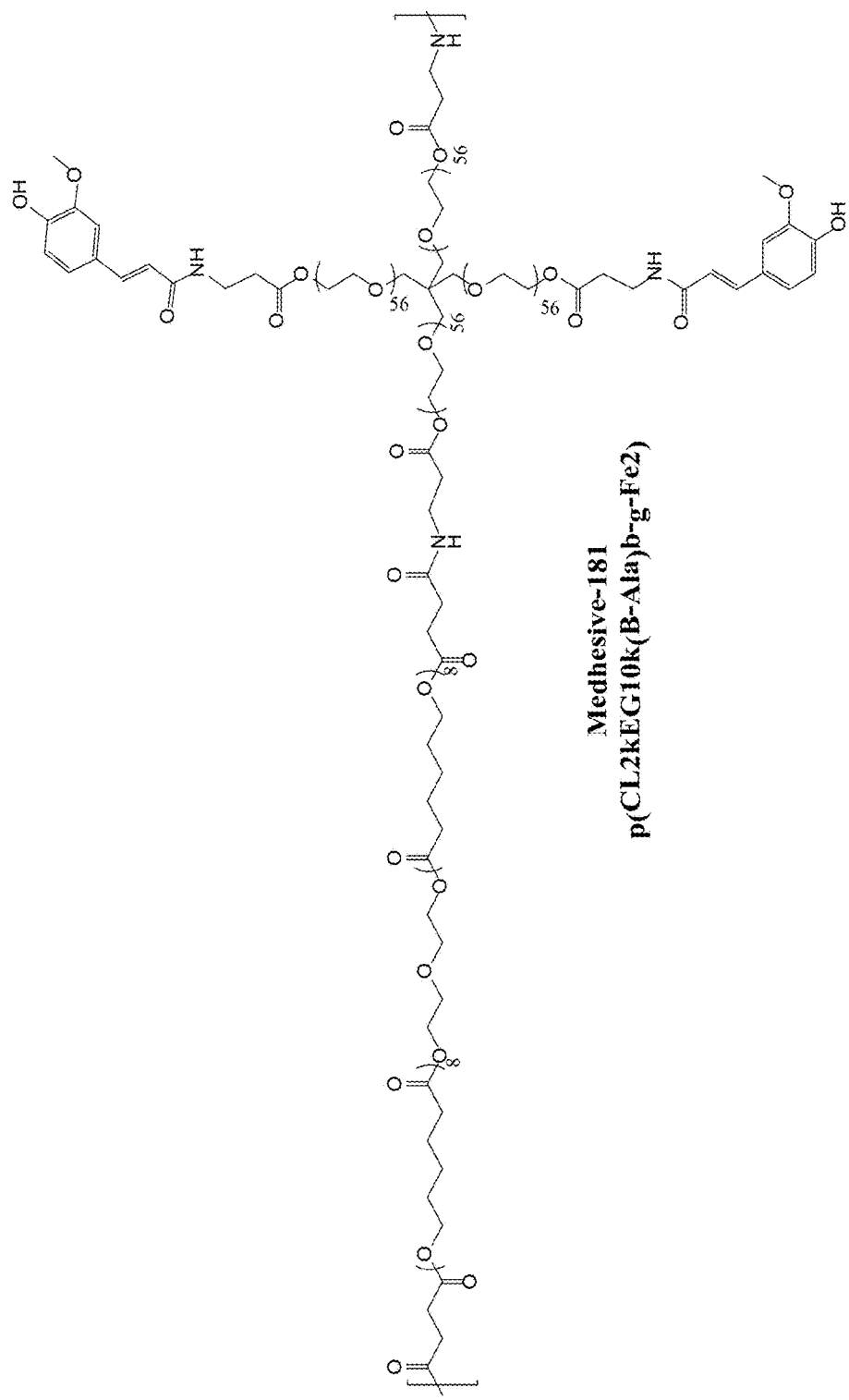
FIG. 8: Depicts general structure of Medhesive-181.
Figure 10:
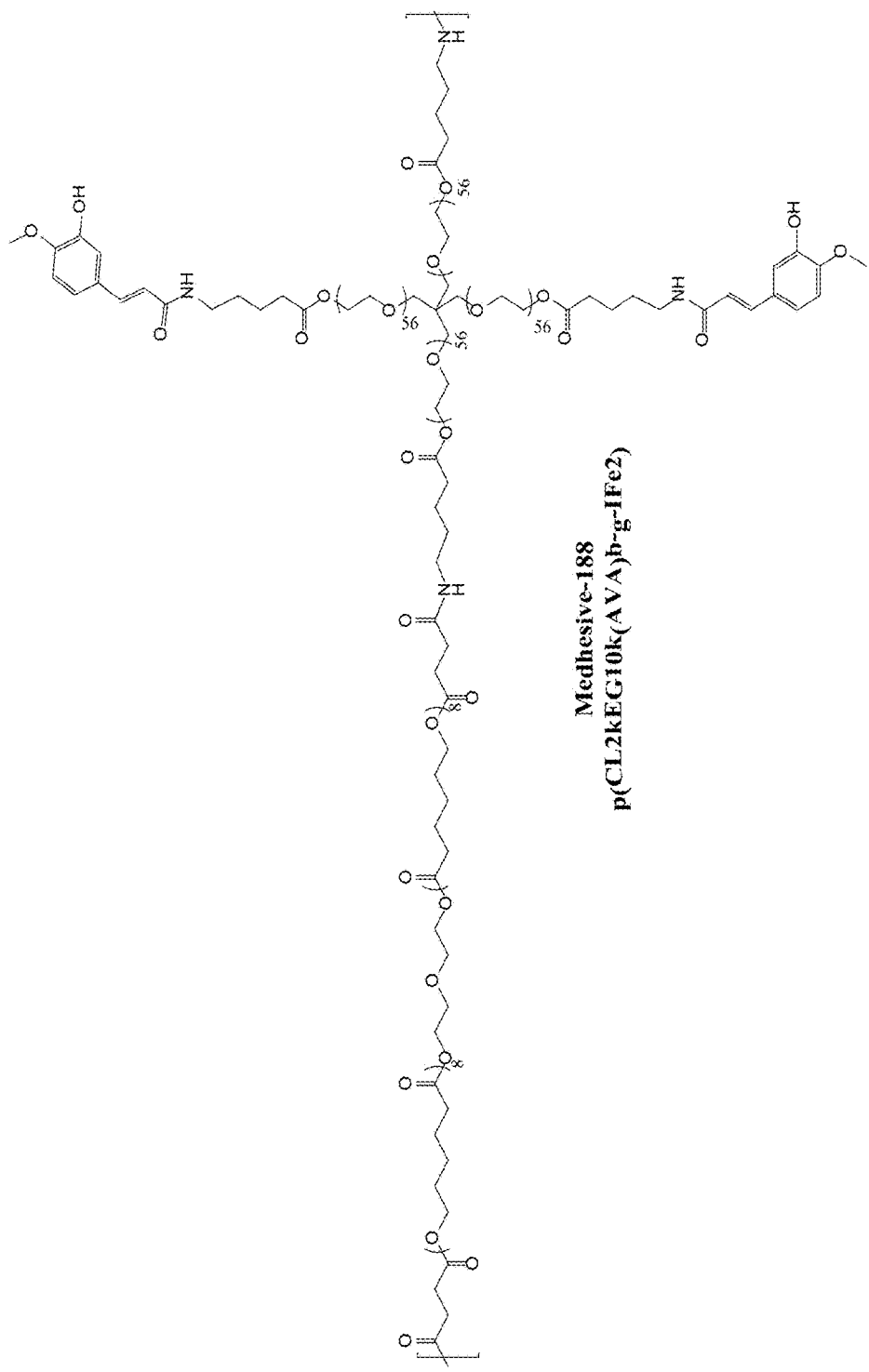
FIG. 10: Depicts general structure of Medhesive-188.
Figure 11:
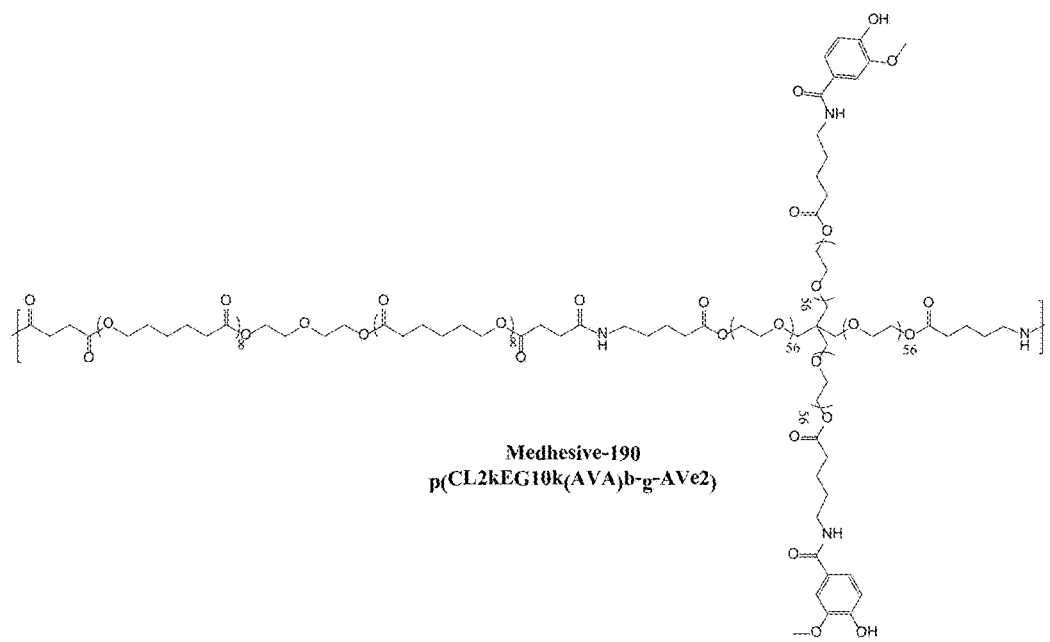
FIG. 11: Depicts general structure of Medhesive-190.
Figure 12:
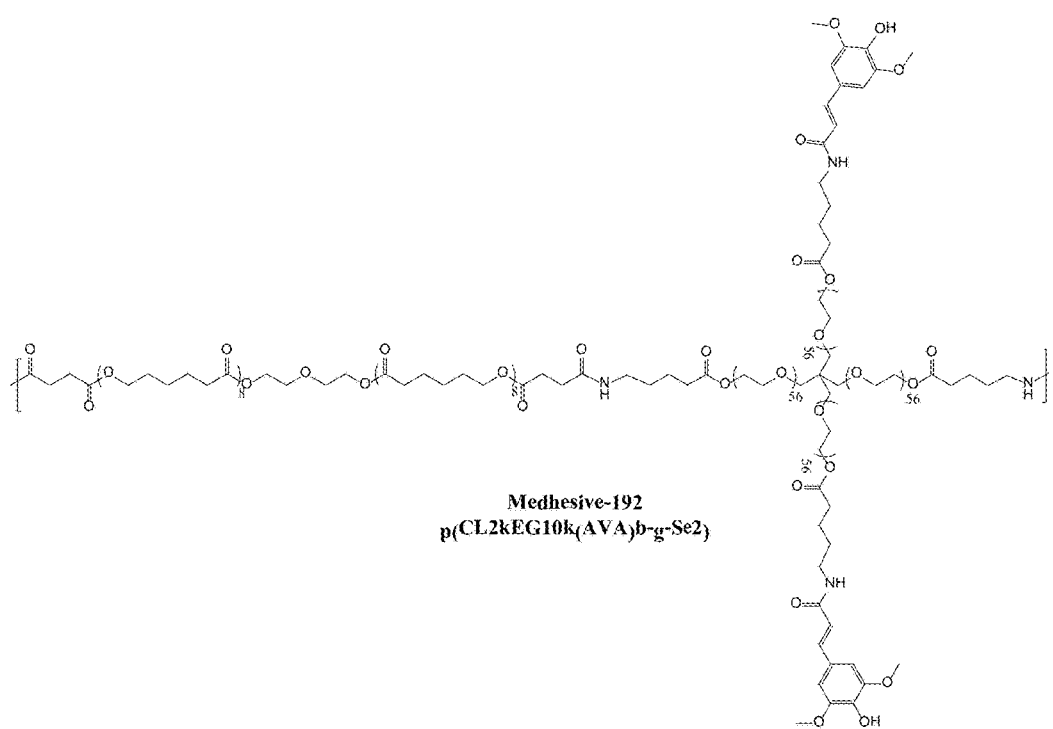
FIG. 12: Depicts general structure of Medhesive-192.
Figure 13:
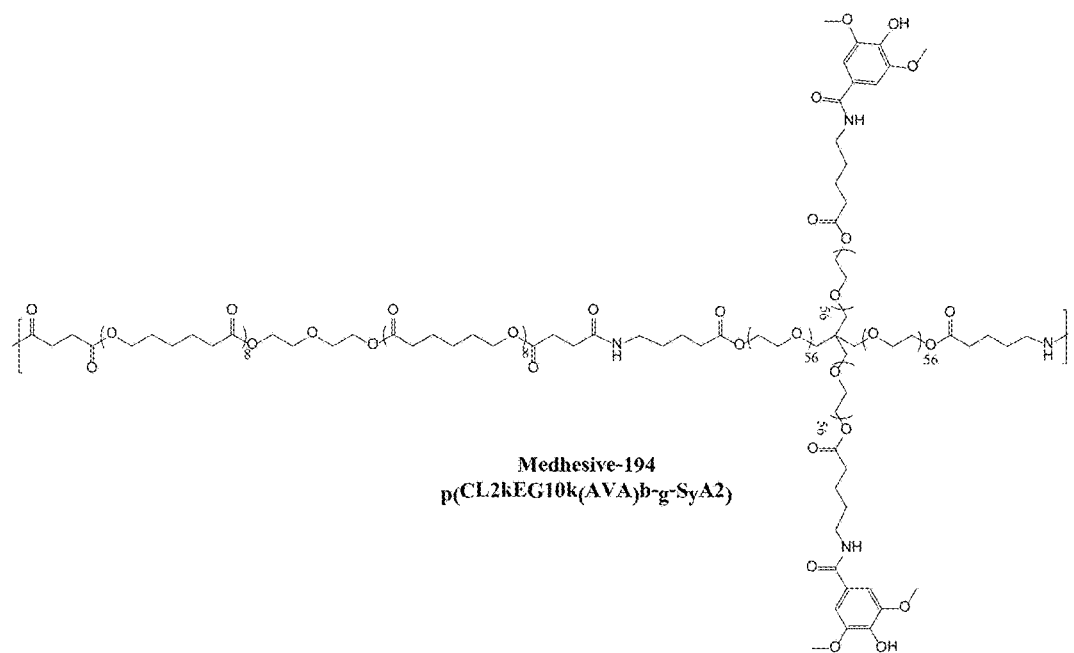
FIG. 13: Depicts general structure of Medhesive-194.
Figure 14:
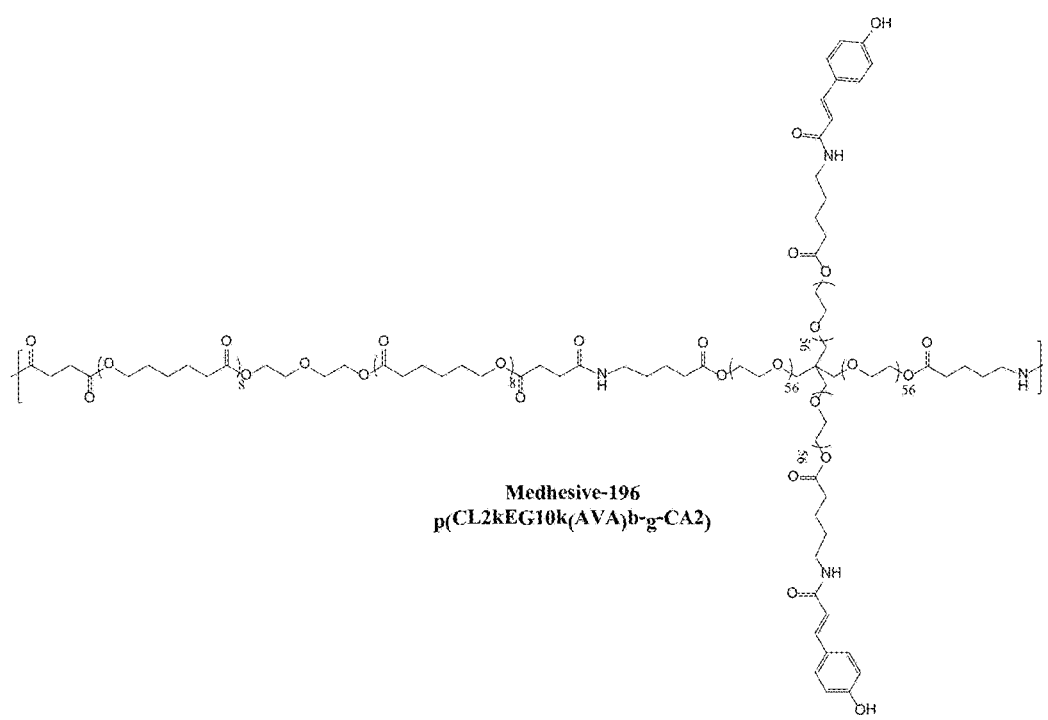
FIG. 14: Depicts general structure of Medhesive-196.
Figure 15:
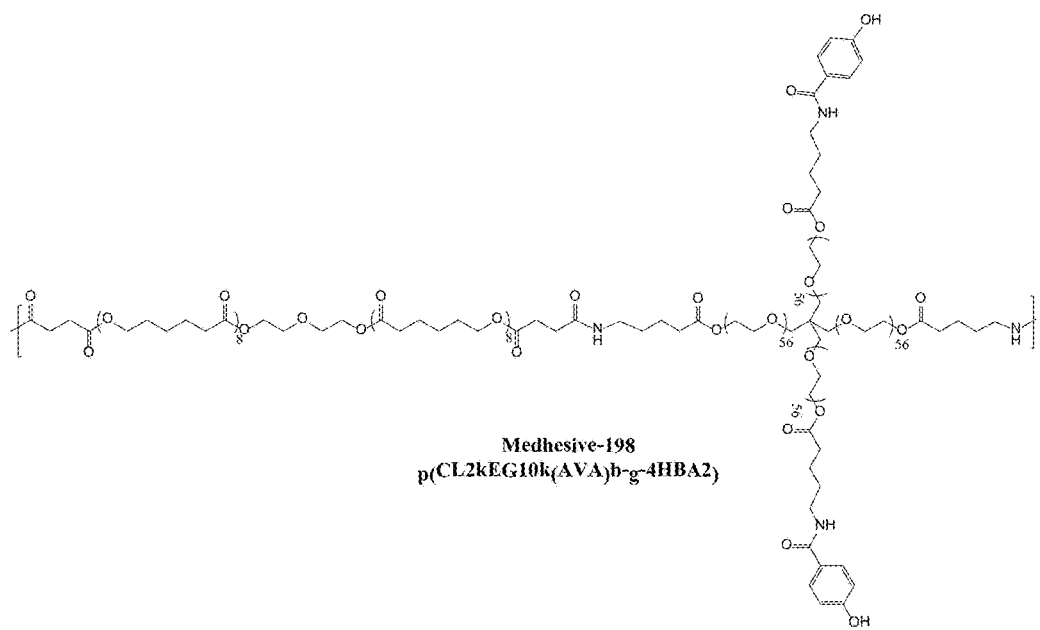
FIG. 15: Depicts general structure of Medhesive-198.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term alkoxy ("OR") is specifically to include groups where R is a hydrogen or alkane chain linked to at least one oxygen.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 15 carbon atoms ($C_1$-$C_{15}$ alkyl), more preferably from 1 to 10 carbon atoms ($C_1$-$C_{10}$ alkyl) and even more preferably from 1 to 6 carbon atoms ($C_1$-$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1-C6 alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The location of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR_cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

The identifier "PA" refers to a poly(alkylene oxide) or substantially poly(alkylene oxide) and means predominantly or mostly alkyloxide or alkyl ether in composition. This definition contemplates the presence of heteroatoms e.g., N, O, S, P, etc. and of functional groups e.g., —COOH, —$NH_2$, —SH, or —OH as well as ethylenic or vinylic unsaturation. It is to be understood any such non-alkyleneoxide structures will only be present in such relative abundance as not to materially reduce, for example, the overall surfactant, non-toxicity, or immune response characteristics, as appropriate, of this polymer. It should also be understood that PAs can include terminal end groups such as PA-O—$CH_2$—$CH_2$—$NH_2$, e.g., PEG-O—$CH_2$—$CH_2$—$NH_2$ (as a common form of amine terminated PA). PA-O—$CH_2$—$CH_2$—$CH_2$—$NH_2$, e.g., PEG-O—$CH_2$—$CH_2$—$CH_2$—$NH_2$ is also available as well as PA-O—$(CH_2$—$CH(CH_3)$—$O)_{xx}$—$CH_2$—$CH(CH_3)$—$NH_2$, where xx is 0 to about 3, e.g., PEG-O—$(CH_2$—$CH(CH_3)$—$O)_{xx}$—$CH_2$—$CH(CH_3)$—$NH_2$ and a PA with an acid end-group typically has a structure of PA-O—$CH_2$—COOH, e.g., PEG-O—$CH_2$—COOH or PA-O—$CH_2$—$CH_2$—COOH, e.g., PEG-O—$CH_2$—$CH_2$—COOH. These can be considered "derivatives" of the PA. These are all contemplated as being within the scope of the invention and should not be considered limiting.

Suitable PAs (polyalkylene oxides) include polyethylene oxides (PEOs), polypropylene oxides (PPOs), polyethylene glycols (PEGs) and combinations thereof that are commercially available from SunBio Corporation, JenKem Technology USA, NOF America Corporation or Creative PEG-Works. It should be understood that, for example, polyethylene oxide can be produced by ring opening polymerization of ethylene oxide as is known in the art.

In one embodiment, the PA can be a block copolymer of a PEO and PPO or a PEG or a triblock copolymer of PEO/PPO/PEO.

Suitable MW ranges of the PA's are from about 300 to about 8,000 daltons, 400 to about 5,000 daltons or from about 450 to about 3,500 daltons.

It should be understood that the PA terminal end groups can be functionalized. Typically the end groups are OH, $NH_2$, COOH, or SH. However, these groups can be converted into a halide (Cl, Br, I), an activated leaving group, such as a tosylate or mesylate, an ester, an acyl halide, N-succinimidyl carbonate, 4-nitrophenyl carbonate, and chloroformate with the leaving group being N-hydroxy succinimide, 4-nitrophenol, and Cl, respectively. etc.

The notation of "L" refers to either a linker or a linking group. A "linker" refers to a moiety that has two points of attachment on either end of the moiety. For example, an alkyl dicarboxylic acid HOOC-alkyl-COOH (e.g., succinic acid) would "link" a terminal end group of a PA (such as a hydroxyl or an amine to form an ester or an amide respectively) with a reactive group of the PD (such as an $NH_2$, OH, or COOH). Suitable linkers include an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a monocyclic or polycyclic heteroaryl bridge (e.g., [3,4]furano [2,3]furano, pyridino, thiopheno, piperidino, piperazino, pyrazidino, pyrrolidino, and the like) or combinations of such bridges, dicarbonyl alkylenes, etc. Suitable dicarbonyl alkylenes include, C2 through C15 dicarbonyl alkylenes such as malonic acid, succinic acid, etc. Additionally, the anhydrides, acid halides and esters of such materials can be used to effect the linking when appropriate and can be considered "activated" dicarbonyl compounds.

Other suitable linkers include moieties that have two different functional groups that can react and link with an end group of a PA. These include groups such as amino acids (glycine, lysine, aspartic acid, etc.), PA's as described herein, poly(ethyleneglycol) bis(carboxymethyl)ethers, polyesters such as polylactides, lactones, polylactones such as polycaprolactone, lactams, polylactams such as polycaprolactam, polyglycolic acid (PGLA), moieties such as tyramine or dopamine and random or block copolymers of 2 or more types of polyesters.

Linkers further include compounds comprising the formula $Y_4$—$R_{17}$—C(=O)—$Y_6$, wherein $Y_4$ is OH, NHR, a halide, or an activated derivative of OH or NHR; $R_{17}$ is a branched or unbranched C1-C15 alkyl group; and $Y_6$ is NHR, a halide, or OR, wherein R is defined above. The term "activated derivative" refers to moieties that make the hydroxyl or amine more susceptible to nucleophilic displacement or for condensation to occur. For example, a hydroxyl group can be esterified by various reagents to provide a more active site for reaction to occur.

A linking group refers to the reaction product of the terminal end moieties of the PA and PD (the situation where "b" is 0; no linker present) condense to form an amide, ether, ester, urea, carbonate or urethane linkage depending on the reactive sites on the PA and PD. In other words, a direct bond is formed between the PA and PD portion of the molecule and no linker is present.

The term "residue" is used to mean that a portion of a first molecule reacts (e.g., condenses or is an addition product via a displacement reaction) with a portion of a second molecule to form, for example, a linking group, such an amide, ether, ester, urea, carbonate or urethane linkage depending on the reactive sites on the PA and PD. This can be referred to as "linkage".

The denotation "PD" refers to a phenolic derivative, such as a mono-hydroxy, mono- or di-methoxy phenyl derivative, for example, a 3-methoxy-4-hydroxy phenyl moiety, or 3,5-dimethoxy-4-hydroxy phenyl moiety. Suitable PD derivatives include the formula:

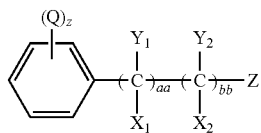

wherein Q is an OH or OCH3;
"z" is 1 to 5;
Each $X_1$, independently, is H, $NH_2$, OH, or COOH;
Each $Y_1$, independently, is H, $NH_2$, OH, or COOH;
Each $X_2$, independently, is H, $NH_2$, OH, or COOH;
Each $Y_2$, independently, is H, $NH_2$, OH, or COOH;
Z is COOH, $NH_2$, OH or SH;
aa is a value of 0 to about 4;
bb is a value of 0 to about 4; and
Optionally provided that when one of the combinations of $X_a$ and $X_2$, $Y_1$ and $Y_2$, $X_1$ and $Y_2$ or $Y_1$ and $X_2$ are absent, then a double bond is formed between the $C_{aa}$ and $C_{bb}$, further provided that aa and bb are each at least 1 to form the double bond when present.

EXPERIMENTAL EXAMPLES

Example 1: Synthesis of PCL1.25 k-diSA 10 g of polycaprolactone-diol (PCL-diol, MW=1,250, 8 mmol), 8 g of succinic anhydride (SA, 80 mmol), 6.4 mL of pyridine (80 mmol), and 100 mL of chloroform were added to a round bottom flask (250 mL). The solution was refluxed in a 75-85° C. oil bath with Ar purging for overnight. The reaction mixture was allowed to cool to room temperature and 100 mL of chloroform was added. The mixture was washed successively with 100 mL each of 12.1 mM HCl, saturated NaCl, and deionized water. The organic layer was dried over magnesium sulfate and then the volume of the mixture was reduced by half by rotary evaporator. After pouring the mixture into 800 mL of a 1:1 hexane and diethyl ether, the polymer was allowed to precipitate at 4° C. for overnight. The polymer was collected and dried under vacuum to yield 8.1 g of PCL1.25 k-diSA. $^1$H NMR (400 MHz, DMSO/TMS): δ 12.2 (s, 1H, COOH—), 4.1 (s, 2H, PCL-CO—$CH_2$—$CH_2$—COOH—) 4.0 (s, 12H, O—(CO—$CH_2$—$(CH_2)_4$—O)$_6$CO—$CH_2$—$CH_2$—COOH), 3.6 (s, 2H, PCL-CO—$CH_2$—$CH_2$—COOH—) 3.3 (s, 2H, —$CH_2$—PCL$_6$-SA), 2.3 (t, 12H, O—(CO—$CH_2$—$(CH_2)_3$—$CH_2$—O)$_6$CO—$CH_2$—$CH_2$—COOH), 1.5 (m, 24H, O—(CO—$CH_2$—$CH_2$—$CH_2$—$CH_2$—$CH_2$—O)$_6$CO—$CH_2$—$CH_2$—COOH), 1.3 (m, 12H, O—(CO—$CH_2$—$CH_2$—$CH_2$—$CH_2$—$CH_2$—O)$_6$CO—$CH_2$—$CH_2$—COOH).

Example 2: Synthesis of PCL2k-diSA (LN011732)

100 g of polycaprolactone-diol (PCL-diol, MW=2,000, 50 mmol) was dissolved in a 1 L round bottom flask while purging under nitrogen. Once completely dissolved, 50 g of succinic anhydride (SA, 500 mmol) was added followed by the addition of 70 mL of triethylamine (502 mmol). The reaction was allowed to react under nitrogen with stirring for ~24 hours. The reaction was cooled in an ice bath for ~70 minutes. Any solids that remained were filtered using vacuum filtration. The round bottom flask was rinsed with ~50 mL of chloroform and this was filtered as well. The solution was transferred to a separatory funnel. The resulting mixture was washed with 1500 mL of a 380 mM aqueous HCl solution. The organic layer was drained out and the aqueous layer was discarded. The organic layer was again transferred to the separatory funnel and washed with 625 mL of nanopure water. The organic layer was drained and the aqueous layer was discarded. The organic layer was again transferred to the separatory funnel and washed with 625 mL of saturated aqueous sodium chloride. The organic layer was drained into an Erlenmeyer flask and the aqueous layer was discarded. To the organic layer was added ~50 g of anhydrous sodium sulfate. The solution was capped and the flask was swirled vigorously by hand for 10 minutes. The sodium sulfate was removed by suction filtration and washed with 50 mL of chloroform. The reaction was poured into 4.05 L of a 2:1 Heptane to MTBE solution and placed at ~4° C. for ~24 hours. The precipitate was collected through vacuum filtration and washed 3 times with a total of 750 mL of a 2:1 Heptane to MTBE solution. The polymer was dried under vacuum for ~24 hours. The yield was 77.23 g. $^1$H NMR (400 MHz, CDCl3/TMS): δ 4.19 (t, 2H, O—$CH_2$—$CH_2$—O—PCL-), 4.02 (m, 16H, O—(OC—$(CH_2)_4$—$CH_2$—O)$_8$—

CO—CH$_2$—CH$_2$—COOH), 3.65 (t, 2H, O—CH$_2$—CH$_2$—O—PCL-) 2.61 (m, 4H, PCL-OOC—CH$_2$—CH$_2$—COOH), 2.27 (t, 16H, O—(CO—CH$_2$—(CH$_2$)$_4$—O)$_8$—CO—CH$_2$—CH$_2$—COOH), 1.6 (m, 32H, O—(CO—CH$_2$—CH$_2$—CH$_2$—CH$_2$—CH$_2$—O)$_8$—CO—CH$_2$—CH$_2$—COOH), 1.31 (m, 16H, O—(CO—CH$_2$—CH$_2$—CH$_2$—CH$_2$—CH$_2$—O)$_8$—CO—CH$_2$—CH$_2$—COOH).

Example 3: Synthesis of Acetyl Ferulic Acid—LN011859

50 g ($_{25}$7 mmol) of ferulic acid was dissolved in 100 mL (1.24 mol) of pyridine and 100 mL (1.06 mol) of acetic anhydride and allowed to stir for 1 hour. The solution was poured into 1 L of nanopure water and the pH was adjusted to 2 using concentrated HCl. The precipitate was vacuum filtered off and dried under vacuum for ~20 hours. The dry material was heated in 300 mL of methanol until the solution came to a slight boil. The solution was removed from the heat source and placed at 4° C. for 4 hours. The precipitate was suction filtered off, washed with 100 mL of methanol, and placed under vacuum for ~18 hours. The dry material was heated in 300 mL of methanol until the solution came to a slight boil. The solution was removed from the heat source and placed at 4° C. for 7 hours. The precipitate was suction filtered off, washed with 100 mL of methanol, and placed under vacuum for ~48 hours. 51.66 g of material was obtained. $^1$H NMR (400 MHz, DMSO/TMS): δ 12.37 (s, 1H, —COOH—), 7.54 (d, 1H, —CH═CH—COOH), 7.44 (s, 1H, —C$_6$H$_3$—), 7.23 (d, 1H, —C$_6$H$_3$—), 7.07 (d, 1H, —C$_6$H$_3$—), 6.55 (d, 1H, —CH═CH—COOH), 3.79 (s, 1H, —CH$_3$—O—C$_6$H$_3$—), 2.23 (s, 3H, CH$_3$—COO—C$_6$H$_3$—).

Example 4: Synthesis of PEG10k-(GABA)$_4$—LN010828

300 g of PEG10k-(OH)$_4$ (30 mmol) was weighed out and placed in a 2 L round bottom flask. To this was added 675 mL of chloroform. The mixture was capped, placed in a water bath and allowed to stir at ambient temperature while purging with argon. Once dissolved, ~73.2 g of Boc-GABA-OH (360 mmol) was added. In a 1 L beaker, ~74.25 g (360 mmol) of DCC was dissolved in 675 mL of chloroform and then added to the reaction. ~1.47 g (12 mmol) of DMAP was added to the reaction and allowed to stir for 24 hours while purging with nitrogen. The insoluble urea was vacuum filtered off. The polymer solution was transferred to 3 L round bottom flask and purged with argon for 10 minutes. 1275 mL of 4M HCl in dioxane was added to the polymer solution. The reaction was allowed to stir under argon for 30 minutes. Once the reaction was finished, the solvent was evaporated off at 40° C. The polymer was then dissolved in 6 L of nanopure water and placed into 2000 MWCO dialysis membrane. The polymer was dialyzed against 42 L of nanopure water with 6 changes of the dialysate over 20 hours. The polymer solution was suction filtered to remove any insoluble urea. The solution was then frozen and placed on a lyophilizer to dry. 234.11 g of material was obtained. $^1$H NMR (400 MHz, D2O/TMS): δ 4.15 (t, 2H, PEG-O—CH$_2$—CH$_2$—OOC—), 3.8-3.2 (m, 224H, PEG), 2.91 (t, 2H, —OOC—CH$_2$—CH$_2$—CH$_2$—NH$_2$), 2.43 (t, 2H, —OOC—CH$_2$—CH$_2$—CH$_2$—NH$_2$), 1.84 (m, 2H, —OOC—CH$_2$—CH$_2$—CH$_2$—NH$_2$).

Example 5: Synthesis of PEG5k-(AVA)$_4$—LN012436

50 g of PEG10k-(OH)$_4$ (10 mmol) was weighed out and placed in a 500 mL round bottom flask. To this was added 125 mL of chloroform. The mixture was capped, placed in a water bath and allowed to stir at ambient temperature while purging with argon. Once dissolved, ~26.1 g of Boc-AVA-OH (120 mmol) was added. In a 125 mL beaker, ~24.76 g (120 mmol) of DCC was dissolved in 125 mL of chloroform and then added to the reaction. ~0.98 g (8 mmol) of DMAP was added to the reaction and allowed to stir for 24 hours while purging with argon. The insoluble urea was vacuum filtered off. The polymer solution was transferred to 1 L round bottom flask and purged with argon for 10 minutes. 425 mL of 4M HCl in dioxane was added to the polymer solution. The reaction was allowed to stir under argon for 30 minutes. Once the reaction was finished, the solvent was evaporated off at 40° C. with gradual increases in temperature such that the final temperature was 80° C. The polymer was then dissolved in 1 L of nanopure water and placed into 2000 MWCO dialysis membrane. The polymer was dialyzed against 9 L of nanopure water with 18 changes of the dialysate over 48 hours. The polymer solution was suction filtered to remove any insoluble urea. The solution was then frozen and placed on a lyophilizer to dry. 14.41 g of material was obtained. $^1$H NMR (400 MHz, D2O/TMS): δ 4.18 (t, 2H, PEG-O—CH$_2$—CH$_2$—OOC—), 3.8-3.2 (m, 112H, PEG), 2.91 (t, 2H, —OOC—CH$_2$—CH$_2$—CH$_2$—CH$_2$—NH$_2$), 2.38 (t, 2H, —OOC—CH$_2$—CH$_2$—CH$_2$—CH$_2$—NH$_2$), 1.59 (m, 4H, —OOC—CH$_2$—CH$_2$—CH$_2$—CH$_2$—NH$_2$).

Example 6: Synthesis of PEG10k-(AVA)$_4$—LN011861

50 g of PEG10k-(OH)$_4$ (5 mmol) was weighed out and placed in a 250 mL round bottom flask. To this was added 4.4 g (20.2 mmol) of Boc-AVA-OH, 0.247 g (2.02 mmol) of DMAP, and 60 mL of DCM. The mixture was capped, placed in a water bath and allowed to stir at ambient temperature while purging with Argon. Once dissolved, 4.17 g of DCC (20.2 mmol) was dissolved with 15 mL of DCM and added to the reaction mixture. The reaction was allowed to stir while purging with Argon for 20 hours. The insoluble urea was vacuum filtered off. The polymer solution was transferred to 250 mL round bottom flask and purged with argon for 10 minutes. 75 mL of 4M HCl in dioxane were added to the polymer solution. The reaction was allowed to stir under argon for 30 minutes. Once the reaction finished, the solvent was evaporated off at 40° C. with gradual increases till the temperature reached 80° C. The polymer was then placed under vacuum overnight. The resulting polymer was dissolved in 670 mL of nanopure water with impure solids being vacuum filtered off. The polymer was purified with tangential flow filtration, frozen, and then placed on a lyophilizer until dry. 32.71 g of material was obtained. $^1$H NMR (400 MHz, D2O/TMS): δ 4.18 (t, 2H, PEG-O—CH$_2$—CH$_2$—OOC—), 3.8-3.2 (m, 224H, PEG), 2.91 (t, 2H, —OOC—CH$_2$—CH$_2$—CH$_2$—CH$_2$—NH$_2$), 2.38 (t, 2H, —OOC—CH$_2$—CH$_2$—CH$_2$—CH$_2$—NH$_2$), 1.59 (m, 4H, —OOC—CH$_2$—CH$_2$—CH$_2$—CH$_2$—NH$_2$).

Example 7: Synthesis of PEG10k-(β-Ala)4—LN011868

50 g of PEG10k-(OH)4 (5 mmol) was weighed out and placed in a 250 mL round bottom flask. To this was added 3.82 g (20.2 mmol) of Boc-β-Ala-OH, 0.247 g (2.02 mmol) of DMAP, and 60 mL of DCM. The mixture was capped, placed in a water bath and allowed to stir at ambient temperature while purging with Argon. Once dissolved, 4.17 g of DCC (20.2 mmol) was dissolved with 15 mL of DCM and added to the reaction mixture. The reaction was allowed to stir while purging with Argon for 20 hours. The insoluble urea was vacuum filtered off. The polymer solution was transferred to 250 mL round bottom flask and purged with argon for 10 minutes. 75 mL of 4M HCl in dioxane was added to the polymer solution. The reaction was allowed to stir under argon for 30 minutes. Once the reaction was finished, the solvent was evaporated off at 40° C. with gradual increases till the temperature reached 80° C. The resulting polymer was dissolved in 800 mL of nanopure water and concentrated to 600 mL. The polymer was purified with tangential flow filtration, frozen, and then placed on a lyophilizer until dry.

33.28 g of material was obtained. $^1$H NMR (400 MHz, D2O/TMS): δ 4.22 (t, 2H, PEG-O—CH$_2$—CH$_2$—OOC—), 3.8-3.25 (m, 224H, PEG), 3.2 (t, 2H, —OOC—CH$_2$—CH$_2$—NH$_2$), 2.75 (t, 2H, —OOC—CH$_2$—CH$_2$—NH$_2$).

Example 8: Synthesis of
Medhesive-145—JLM-664-06

7.34 g (3.4 mmol) of PCL2k-diSA, 35 g (3.34 mmol) of PEG10k-(GABA)4, and 1.98 g (8.34 mmol) of Acetyl Ferulic Acid were dissolved in 275 mL DMF and 200 mL of chloroform. 6.34 g (16.69 mmol) of HBTU was dissolved in 255 mL of DMF. The HBTU solution was then added to the reaction mixture along with 3.23 mL (23.19 mmol) of triethylamine. The reaction was allowed to stir for 2 hours. 1.58 g (6.68 mmol) of Acetyl Ferulic Acid was added to the reaction followed by 0.70 mL (5.03 mmol) of triethylamine. The reaction was allowed to stir for another hour. The reaction was poured into 4 L of a 1:1 Heptane-to-MTBE mix and placed at 4° C. for 24 hours. The precipitate was removed and dried under vacuum for 24 hours (called polymer Medhesive-159). Once dry, the polymer (Medhesive-159), was dissolved in 550 mL of chloroform and purged with argon for at least 10 minutes. 90 mL of piperidine was added to the polymer solution. The reaction was allowed to proceed with stirring while purging with argon, for 45 minutes. The polymer was poured into 3.4 L of a 1:1 Heptane-to-MTBE solution and placed at −15 C. for ~20 hours. The precipitate was suction filtered off and placed under vacuum for 3 days. The polymer was dissolved with 675 mL of methanol and placed into 15000 MWCO dialysis membrane. The polymer solution was dialyzed against 9 L of nanopure water, acidified with 0.9 mL of concentrated HCl. 10 changes of dialysate were made over ~43 hours. The dialysate was changed to 9 L of nanopure water and changed 5 times over the next 5 hours. The polymer was frozen and freeze dried until dry. 37.5 g of material was obtained. UV-VIS Wt % FA=3.05+/−0.05%, 0.159+/−0.003 umol FA/mg polymer; DSC ($2^{nd}$ heat) =40.87° C.

Example 9: Synthesis of
Medhesive-179—JLM-664-48

6.853 g (3.12 mmol) of PCL2k-diSA, 32.6 g (3.11 mmol) of PEG10k-(AVA)$_4$, and 1.847 g (7.82 mmol) of Acetyl Ferulic Acid were dissolved in 250 mL DMF and 185 mL of chloroform. 5.899 g (15.56 mmol) of HBTU was dissolved in 250 mL of DMF. The HBTU solution was then added to the reaction mixture along with 3.01 mL (21.6 mmol) of triethylamine. The reaction was allowed to stir for 2 hours. 1.479 g (6.26 mmol) of Acetyl Ferulic Acid was added to the reaction followed by 0.653 mL (4.69 mmol) of triethylamine. The reaction was allowed to stir for another hour. The reaction was poured into 4 L of a 1:1 Heptane-to-MTBE mix and placed at 4° C. for 16 hours. The precipitate was removed and dried under vacuum for 6 hours (called polymer Medhesive-178). Once dry, the polymer (Medhesive-178), was dissolved in 325 mL of chloroform and purged with argon for at least 10 minutes. 65 mL of piperidine was added to the polymer solution. The reaction was allowed to proceed with stirring while purging with argon, for 45 minutes. The polymer was poured into 3.2 L of a 1:1 Heptane-to-MTBE solution and placed at 4° C. for ~20 hours. The precipitate was suction filtered off and placed under vacuum for 22 hours. The polymer was dissolved with 550 mL of methanol and placed into 15000 MWCO dialysis membrane. The polymer solution was dialyzed against 9 L of nanopure water, acidified with 0.9 mL of concentrated HCl. 10 changes of dialysate were made over ~44 hours. The dialysate was changed to 9 L of nanopure water and changed 5 times over the next 6 hours. The polymer was frozen and freeze dried until dry. 36.19 g of material was obtained; DSC ($2^{nd}$ heat)=40.09+/−0.07° C.; IV=1.2+/−0.021 dl/g Example 10: Synthesis of
Medhesive-181—LN011885

7.04 g (3.2 mmol) of PCL2k-diSA, 33.31 g (3.17 mmol) of PEG10k-(β-Ala)$_4$, and 1.89 g (8.0 mmol) of Acetyl Ferulic Acid were dissolved in 250 mL DMF and 200 mL of chloroform. 6.06 g (15.98 mmol) of HBTU was dissolved in 250 mL of DMF. The HBTU solution was then added to the reaction mixture along with 3.09 mL (22.17 mmol) of triethylamine. The reaction was allowed to stir for 2 hours. 1.51 g (6.39 mmol) of Acetyl Ferulic Acid was added to the reaction followed by 0.670 mL (4.80 mmol) of triethylamine. The reaction was allowed to stir for another hour. The reaction was poured into 4 L of diethyl ether and placed at 4° C. for 19 hours. The precipitate was removed and dried under vacuum for 6 days (called polymer Medhesive-180). Once dry, the polymer (Medhesive-180), was dissolved in 350 mL of chloroform and purged with argon for at least 10 minutes. 67 mL of piperidine was added to the polymer solution. The reaction was allowed to proceed with stirring while purging with argon, for 45 minutes. The polymer was poured into 3.4 L of a 1:1 Heptane-to-MTBE solution and placed at −15° C. for ~18 hours. The precipitate was suction filtered off and placed under vacuum for 5 days. The polymer was dissolved with 450 mL of methanol and placed into 15000 MWCO dialysis membrane. The polymer solution was dialyzed against 7 L of nanopure water, acidified with 0.7 mL of concentrated HCl. 10 changes of dialysate were made over ~47 hours. The dialysate was changed to 9 L of nanopure water and changed 5 times over the next 4 hours. The polymer was frozen and freeze dried until dry. 33.09 g of material was obtained.

Example 11: Synthesis of Acetyl Isoferulic
Acid—JLM-664-92

10.07 g (51.9 mmol) of isoferulic acid was dissolved in 22 mL (273 mmol) of pyridine and 22 mL (233 mmol) of acetic anhydride and allowed to stir for 2 hour. The solution was poured into 500 mL of nanopure water and the pH was adjusted to 2 using concentrated HCl. The precipitate was vacuum filtered off and dried under vacuum for ~20 hours. The dry material was heated in 200 mL of methanol until the solution came to a slight boil. The solution was removed from the heat source and placed at 4° C. for 2 hours. The precipitate was suction filtered off, washed with 100 mL of methanol, and placed under vacuum for ~3 weeks. The dry material was heated in 300 mL of methanol until the solution came to a slight boil. The solution was removed from the heat source and placed at 4° C. for 1 hour. The precipitate was suction filtered off, washed with 100 mL of methanol, and placed under vacuum for ~16 hours. 4.84 g of material was obtained.

Example 12: Synthesis of Acetyl Vanillic Acid—LN011035

20.04 g (112 mmol) of Vanillic Acid was dissolved in 50 mL (618 mmol) of pyridine and 50 mL (529 mmol) of acetic anhydride and allowed to stir for 2 hour. The solution was poured into 1200 mL of nanopure water and the pH was adjusted to 2 using concentrated HCl. The solution was extracted twice with a total of 700 mL of ethyl acetate and dried with anhydrous magnesium sulfate. The magnesium sulfate was suction filtered off and the organic solvent was evaporated off. The compound was dried for ~23 hours under vacuum. The compound was recrystallized in 400 mL of a 1:1 mixture of water:methanol. The precipitate was suction filtered and placed under vacuum. 21.58 g of material was obtained.

Example 13: Synthesis of Acetyl Sinapic Acid—JLM-688-50

14.95 g (66.7 mmol) of Sinapic acid was dissolved in 30 mL (372 mmol) of pyridine and 30 mL (317 mmol) of acetic anhydride and allowed to stir for 2 hour. The solution was poured into 300 mL of nanopure water and the pH was adjusted to 2 using concentrated HCl. The precipitate was vacuum filtered off and dried under vacuum for ~3 hours. The dry material was heated in 150 mL of methanol until the solution came to a slight boil. The solution was removed from the heat source and placed at 4° C. for 1 hour. The precipitate was suction filtered off, washed with 100 mL of methanol, and placed under vacuum for ~16 hours. The dry material was heated in 150 mL of methanol until the solution came to a slight boil. The solution was removed from the heat source and placed at 4° C. for 3 hours. The precipitate was suction filtered off, washed with 100 mL of methanol, and placed under vacuum for ~20 hours. 2.0 g of material was obtained.

Example 14: Synthesis of Acetyl Syringic Acid—JLM-688-52

14.90 g (75.2 mmol) of Syringic acid was dissolved in 30 mL (372 mmol) of pyridine and 30 mL (317 mmol) of acetic anhydride and allowed to stir for 2 hour. The solution was poured into 300 mL of nanopure water and the pH was adjusted to 2 using concentrated HCl. The precipitate was vacuum filtered off and dried under vacuum for ~3 hours. The dry material was heated in 150 mL of methanol until the solution came to a slight boil. 150 mL of nanopure water was added to the solution. The solution was removed from the heat source and placed at 4° C. for 2 hours. The precipitate was suction filtered off, washed with 100 mL of nanopure water, and placed under vacuum for ~15 hours. The dry material was heated in 150 mL of methanol until the solution came to a slight boil. 150 mL of nanopure water was added to the solution. The solution was removed from the heat source and placed at 4° C. for 4 hours. The precipitate was suction filtered off, washed with 100 mL of nanopure water, and placed under vacuum for ~20 hours. 10.54 g of material was obtained.

Example 15: Synthesis of Acetyl p-Coumaric Acid—JLM-688-67

25.03 g (152 mmol) of p-Coumaric Acid was dissolved in 50 mL (620 mmol) of pyridine and 50 mL (529 mmol) of acetic anhydride and allowed to stir for 1.5 hour. The solution was poured into 500 mL of nanopure water and the pH was adjusted to 2 using concentrated HCl. The precipitate was vacuum filtered off and dried under vacuum for ~24 hours. The dry material was heated in 150 mL of methanol until the solution came to a slight boil. 150 mL of nanopure water was added to the solution. The solution was removed from the heat source and placed at 4° C. for 17 hours. The precipitate was suction filtered off, washed with 150 mL of nanopure water, and placed under vacuum for ~24 hours. The dry material was heated in 150 mL of methanol until the solution came to a slight boil. 150 mL of nanopure water was added to the solution. The solution was removed from the heat source and placed at 4° C. for 3 hours. The precipitate was suction filtered off, washed with 150 mL of nanopure water, and placed under vacuum for ~20 hours. 29.73 g of material was obtained.

Example 16: Synthesis of 4-Acetoxybenzoic Acid—JLM-688-64

25.22 g (183 mmol) of 4-Hydroxybenzoic Acid was dissolved in 50 mL (620 mmol) of pyridine and 50 mL (529 mmol) of acetic anhydride and allowed to stir for 1.5 hour. The solution was poured into 500 mL of nanopure water and the pH was adjusted to 2 using concentrated HCl. The precipitate was vacuum filtered off and dried under vacuum for ~24 hours. The dry material was heated in 150 mL of methanol until the solution came to a slight boil. 150 mL of nanopure water was added to the solution. The solution was removed from the heat source and placed at 4° C. for 17 hours. The precipitate was suction filtered off, washed with 150 mL of nanopure water, and placed under vacuum for ~24 hours. The dry material was heated in 150 mL of methanol until the solution came to a slight boil. 150 mL of nanopure water was added to the solution. The solution was removed from the heat source and placed at 4° C. for 3 hours. The precipitate was suction filtered off, washed with 150 mL of nanopure water, and placed under vacuum for ~20 hours. 24.44 g of material was obtained.

Example 17: Synthesis of Medhesive-188—JLM-688-54

3.675 g (1.67 mmol) of PCL2k-diSA, 17.484 g (1.67 mmol) of PEG10k-(AVA)$_4$, and 0.99 g (4.19 mmol) of Acetyl Isoferulic Acid was dissolved in 133 mL DMF and 100 mL of chloroform. 3.16 g (8.33 mmol) of HBTU was dissolved in 133 mL of DMF. The HBTU solution was then added to the reaction mixture along with 1.615 mL (11.59 mmol) of triethylamine. The reaction was allowed to stir for 2 hours. 0.794 g (3.36 mmol) of Acetyl Isoferulic Acid was added to the reaction followed by 0.350 mL (2.51 mmol) of triethylamine. The reaction was allowed to stir for another hour. The reaction was poured into 3.2 L of a 1:1 Heptane-to-MTBE solution and placed at 4° C. for 23 hours. The precipitate was removed and dried under vacuum for 3 days (called polymer Medhesive-187). Once dry, the polymer (Medhesive-187), was dissolved in 180 mL of chloroform and purged with argon for at least 10 minutes. 40 mL of piperidine was added to the polymer solution. The reaction was allowed to proceed with stirring while purging with argon, for 45 minutes. The polymer was poured into 1.8 L of a 1:1 Heptane-to-MTBE solution and placed at −15° C. for ~20 hours. The precipitate was suction filtered off and placed under vacuum for 25 hours. The polymer was dissolved with 280 mL of methanol and placed into 15000 MWCO dialysis membrane. The polymer solution was dialyzed against 5 L of nanopure water, acidified with 0.5 mL of concentrated HCl. 10 changes of dialysate were made over ~45 hours. The dialysate was changed to 5 L of nanopure water and changed 5 times over the next 4 hours. The polymer was frozen and freeze dried until dry. 18.66 g of material was obtained.

Example 18: Synthesis of Medhesive-190—JLM-688-57

1.832 g (0.83 mmol) of PCL2k-diSA, 8.737 g (0.83 mmol) of PEG10k-(AVA)$_4$, and 0.439 g (2.09 mmol) of Acetyl Vanillic Acid was dissolved in 67 mL DMF and 50 mL of chloroform. 1.587 g (4.19 mmol) of HBTU was dissolved in 67 mL of DMF. The HBTU solution was then added to the reaction mixture along with 0.81 mL (5.81 mmol) of triethylamine. The reaction was allowed to stir for 2 hours. 0.359 g (1.71 mmol) of Acetyl Vanillic Acid was added to the reaction followed by 0.175 mL (1.26 mmol) of triethylamine. The reaction was allowed to stir for another hour. The reaction was poured into 1.6 L of a 1:1 Heptane-to-MTBE solution and placed at 4° C. for 3 days. The precipitate was removed and dried under vacuum for 3 days (called polymer Medhesive-189). Once dry, the polymer (Medhesive-189), was dissolved in 90 mL of chloroform and purged with argon for at least 10 minutes. 20 mL of piperidine was added to the polymer solution. The reaction was allowed to proceed with stirring while purging with argon, for 45 minutes. The polymer was poured into 900 mL of a 1:1 Heptane-to-MTBE solution and placed at −15° C. for ~20 hours. The precipitate was suction filtered off and placed under vacuum for 25 hours. The polymer was dissolved with 145 mL of methanol and placed into 15000 MWCO dialysis membrane. The polymer solution was dialyzed against 2.5 L of nanopure water, acidified with 0.25 mL of concentrated HCl. 10 changes of dialysate were made over ~45 hours. The dialysate was changed to 2.5 L of nanopure water and changed 5 times over the next 4 hours. The polymer was frozen and freeze dried until dry. 9.56 g of material was obtained.

Example 19: Synthesis of Medhesive-192—JLM-688-74

3.147 g (1.43 mmol) of PCL2k-diSA, 15.03 g (1.43 mmol) of PEG10k-(AVA)$_4$, and 0.953 g (3.58 mmol) of Acetyl Sinapic Acid was dissolved in 115 mL DMF and 85 mL of chloroform. 2.722 g (7.18 mmol) of HBTU was dissolved in 115 mL of DMF. The HBTU solution was then added to the reaction mixture along with 1.38 mL (9.9 mmol) of triethylamine. The reaction was allowed to stir for 2 hours. 0.76 g (2.85 mmol) of Acetyl Sinapic Acid was added to the reaction followed by 0.3 mL (2.15 mmol) of triethylamine. The reaction was allowed to stir for another hour. The reaction was poured into 2.4 L of a 1:1 Heptane-to-MTBE solution and placed at 4° C. for 15 hours. The precipitate was removed and dried under vacuum for 17 hours (called polymer Medhesive-191). Once dry, the polymer (Medhesive-191), was dissolved in 150 mL of chloroform and purged with argon for at least 10 minutes. 36 mL of piperidine was added to the polymer solution. The reaction was allowed to proceed with stirring while purging with argon, for 45 minutes. The polymer was poured into 1.7 L of a 1:1 Heptane-to-MTBE solution and placed at −15° C. for ~23 hours. The precipitate was suction filtered off and placed under vacuum for 2 days. The polymer was dissolved with 240 mL of methanol and placed into 15000 MWCO dialysis membrane. The polymer solution was dialyzed against 5 L of nanopure water, acidified with 0.5 mL of concentrated HCl. 10 changes of dialysate were made over ~45 hours. The dialysate was changed to 5 L of nanopure water and changed 5 times over the next 4 hours. The polymer was frozen and freeze dried until dry. 14.95 g of material was obtained.

Example 20: Synthesis of Medhesive-194—JLM-688-71

3.15 g (1.43 mmol) of PCL2k-diSA, 14.99 g (1.43 mmol) of PEG10k-(AVA)$_4$, and 0.867 g (3.61 mmol) of Acetyl Syringic Acid was dissolved in 115 mL DMF and 85 mL of chloroform. 2.714 g (7.16 mmol) of HBTU was dissolved in 115 mL of DMF. The HBTU solution was then added to the reaction mixture along with 1.38 mL (9.9 mmol) of triethylamine. The reaction was allowed to stir for 2 hours. 0.69 g (2.87 mmol) of Acetyl Syringic Acid was added to the reaction followed by 0.3 mL (2.15 mmol) of triethylamine. The reaction was allowed to stir for another hour. The reaction was poured into 2.4 L of a 1:1 Heptane-to-MTBE solution and placed at 4° C. for 15 hours. The precipitate was removed and dried under vacuum for 17 hours (called polymer Medhesive-193). Once dry, the polymer (Medhesive-193), was dissolved in 150 mL of chloroform and purged with argon for at least 10 minutes. 36 mL of piperidine was added to the polymer solution. The reaction was allowed to proceed with stirring while purging with argon, for 45 minutes. The polymer was poured into 1.7 L of a 1:1 Heptane-to-MTBE solution and placed at −150 C. for ~23 hours. The precipitate was suction filtered off and placed under vacuum for 2 days. The polymer was dissolved with 240 mL of methanol and placed into 15000 MWCO dialysis membrane. The polymer solution was dialyzed against 5 L of nanopure water, acidified with 0.5 mL of concentrated HCl. 10 changes of dialysate were made over ~45 hours. The dialysate was changed to 5 L of nanopure water and changed 5 times over the next 4 hours. The polymer was frozen and freeze dried until dry. 16.07 g of material was obtained.

Example 21: Synthesis of Medhesive-196—JLM-688-81

1.378 g (0.626 mmol) of PCL2k-diSA, 6.56 g (0.626 mmol) of PEG10k-(AVA)$_4$, and 0.325 g (1.58 mmol) of 4-Acetyl Coumaric Acid is dissolved in 50 mL DMF and 40 mL of chloroform. 1.204 g (3.18 mmol) of HBTU is dissolved in 50 mL of DMF. The HBTU solution is then added to the reaction mixture along with 0.605 mL (4.34 mmol) of triethylamine. The reaction is allowed to stir for 2 hours. 0.256 g (1.24 mmol) of 4-Acetyl Coumaric Acid is added to the reaction followed by 0.131 mL (0.94 mmol) of triethylamine. The reaction is allowed to stir for another hour. The reaction is poured into 800 mL of a 1:1 Heptane-to-MTBE solution and placed at 4° C. for 16 hours. The precipitate is removed and dried under vacuum for 17 hours (called polymer Medhesive-195). Once dry, the polymer (Medhesive-195), is dissolved in 70 mL of chloroform and purged with argon for at least 10 minutes. 17 mL of piperidine is added to the polymer solution. The reaction is allowed to proceed with stirring while purging with argon, for 45 minutes. The polymer is poured into 800 mL of a 1:1 Heptane-to-MTBE solution and placed at −15° C. for ~24 hours. The precipitate is suction filtered off and placed under vacuum for 2 days. The polymer is dissolved with 110 mL of methanol and placed into 15000 MWCO dialysis membrane. The polymer solution is dialyzed against 3 L of nanopure water, acidified with 0.3 mL of concentrated HCl. 10 changes of dialysate are made over ~45 hours. The dialysate is changed to 3 L of nanopure water and changed 5 times over the next 4 hours. The polymer is frozen and freeze dried until dry.

Example 22: Synthesis of Medhesive-198—JLM-688-84

1.379 g (0.627 mmol) of PCL2k-diSA, 6.58 g (0.627 mmol) of PEG10k-(AVA)$_4$, and 0.285 g (1.58 mmol) of 4-Acetoxybenzoic Acid is dissolved in 50 mL DMF and 40 mL of chloroform. 1.201 g (3.17 mmol) of HBTU is dissolved in 50 mL of DMF. The HBTU solution is then added to the reaction mixture along with 0.605 mL (4.34 mmol) of triethylamine. The reaction is allowed to stir for 2 hours. 0.228 g (1.27 mmol) of 4-Acetoxybenzoic Acid is added to the reaction followed by 0.131 mL (0.94 mmol) of triethylamine. The reaction is allowed to stir for another hour. The reaction is poured into 800 mL of a 1:1 Heptane-to-MTBE solution and placed at 4° C. for 16 hours. The precipitate is removed and dried under vacuum for 17 hours (called polymer Medhesive-197). Once dry, the polymer (Medhesive-197), is dissolved in 70 mL of chloroform and purged with argon for at least 10 minutes. 17 mL of piperidine is added to the polymer solution. The reaction is allowed to proceed with stirring while purging with argon, for 45 minutes. The polymer is poured into 800 mL of a 1:1 Heptane-to-MTBE solution and placed at −15° C. for ~24 hours. The precipitate is suction filtered off and placed under vacuum for 2 days. The polymer is dissolved with 110 mL of methanol and placed into 15000 MWCO dialysis membrane. The polymer solution is dialyzed against 3 L of nanopure water, acidified with 0.3 mL of concentrated HCl. 10 changes of dialysate are made over ~45 hours. The dialysate is changed to 3 L of nanopure water and changed 5 times over the next 4 hours. The polymer is frozen and freeze dried until dry.

Example 23: Mono-Layered Thin Film Adhesives

Figure 16:
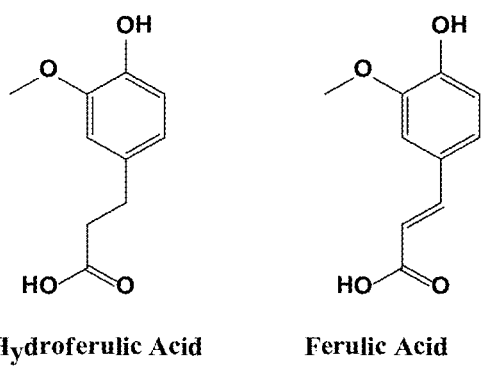
FIG. 16: Shows hydroferulic acid and ferulic acid.

Switching the hydroferulic acid adhesive moiety to ferulic acid (FIG. 16) in a bi-layer formulation increases the stability of the film. It has been found that using novel adhesive moieties, oxidants may be added directly into the adhesive film using existing solvent casting methods without observing significant preoxidation. Solvents used consisted of a mixture of methanol and chloroform which evaporated off in ~30-45 minutes. The resulting film was opaque with a slight yellow color. The material only begins to lose its ability to adhere to tissue surfaces when it has turned a deep brown.

Example 24: Mono-Layered Thin Film Adhesives Able to Undergo Sterilization

Figure 17:
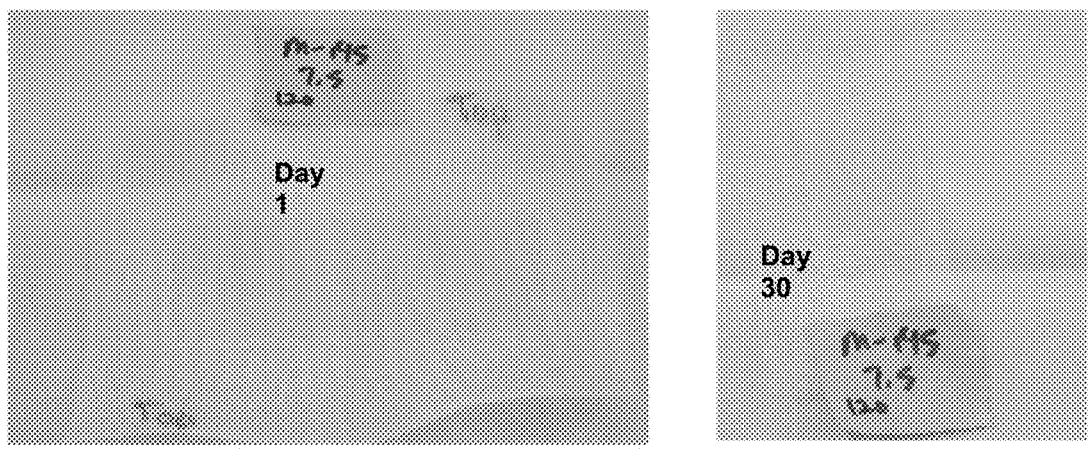
FIG. 17: Shows Medhesive-145 at a 1.5:1 $NaIO_4$:Ferulic Acid molar ratio coated at 120 g/m$^2$ and stored at room temperature at Day 1 and Day 30.
Figure 18:
FIG. 18: Shows Medhesive-145 at a 1.38:1 $NaIO_4$:Ferulic Acid molar ratio with a coating density of 90 g/m$^2$. Samples stored in double pouched Tyvek at ambient temperatures. A) Unsterilized, B) and C) E-Beam Sterilized at 25 kGy.

By switching the hydroferulic acid of the adhesive thin film with ferulic acid the oxidant could be directly incorporated into the thin film. Additionally, it was shown that these films were stable over a period of 30 days (FIG. 17). Further monitoring of these films over time has shown that they may be stored at ambient condition up to ~4 months without significant color change. The films may undergo sterilization without any visible activation. Ferulic acid containing polymers offer the ability to create a mono-layered film able to undergo sterilization while at the same time improving stability.

Example 25: Polymer Synthesis

Polymers have been synthesized to increase mechanical performance, and to slow degradation profiles by varying the degradable ester linkage in the adhesive polymer. By increasing and varying the polyester content of the adhesive film, the lap shear performance of the thin film construct may be increased. Medhesive-179, 163, and 165 were synthesized to measure the effect of increasing polycaprolactone content on the lap shear results (Table 1). Additionally, Medhesive-177, 167, and 169, which contain polylactic acid, were tested to observe the difference between polyester material as well as the effect of higher polylactic acid content (Table 1). Medhesive-171 was synthesized to measure the effect of increasing the ferulic acid concentration (Table 1). Medhesive-145 and Medhesive-179 consist of two degradation profiles useful in determining the duration the adhesive must be present in vivo to be effective (Table 1).

TABLE 1

Proposed Compounds to Synthesize and Relative Wt % Components;

| Compound | FA Wt % | PCL Wt % | PLA Wt % | PEG Wt % | Acc Deg. (55° C.) |
|---|---|---|---|---|---|
| Med-145 | 2.73% | 16.86% | — | 80.41% | 14-15 days |
| Med-177 | 2.73% | — | 16.86% | 80.41% | |
| Med-179 | 2.73% | 16.86% | — | 80.41% | 18-19 days |
| Med-163 | ~3% | ~53%% | — | ~44% | |
| Med-167 | ~3% | — | ~53% | ~44% | |
| Med-165 | ~3.2% | ~75% | — | ~22% | |
| Med-169 | ~3.2% | — | ~75% | ~22% | |
| Med-171 | 4.96% | 17.60% | — | 77.44% | |

Acc. Deg. = Accelerated degradation at 55° C. in 1x PBS buffer (pH = 7.4)

Medhesive-163 and Medhesive-165 contain a significant amount of tin (2.5-5 wt %) associated with the polymerization process of the PCL. Because of this, their lower synthetic yields and the fact that they either did not have good lap shear results (M-163) or did not form a workable thin film (M-165), the two polymers were discarded from further development. Medhesive-167 was synthesized in low yield and had a low transition temperature which made it overly tacky. The tackiness made it difficult to handle and therefore unsuitable in a medical settings. Additionally, lap shear results indicate it had poor adhesive qualities when activated. A similar profile was noticed with Medhesive-171. As such these 2 polymers are not selected for further development.

Figure 19:
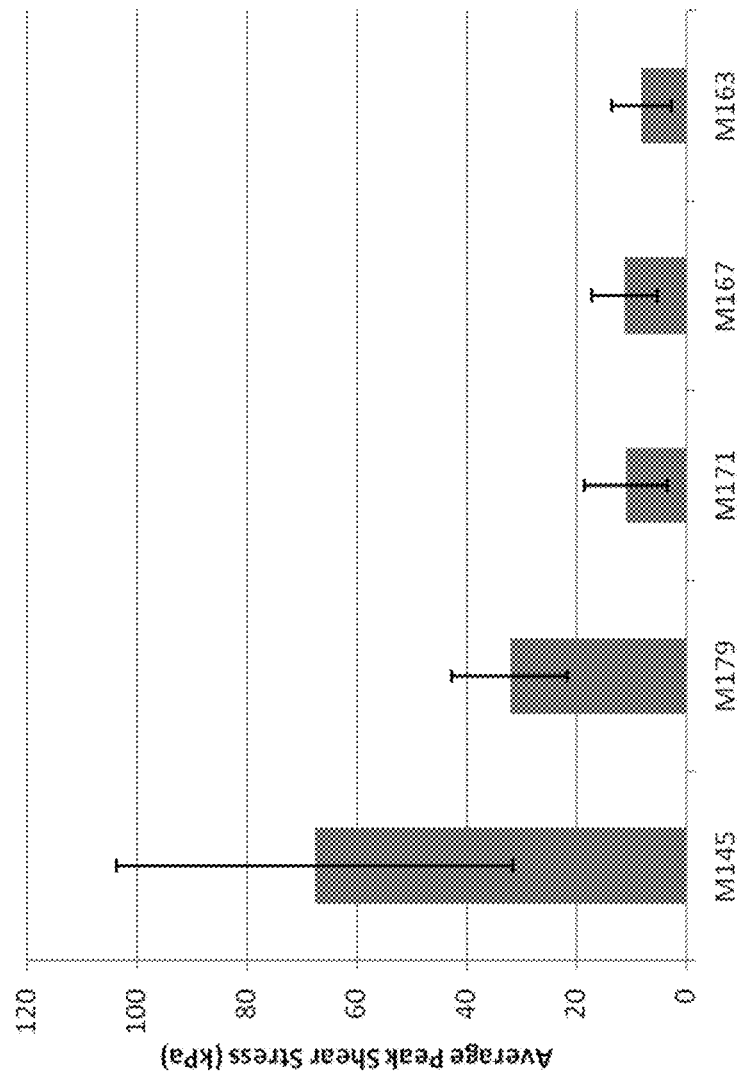
FIG. 19: Shows lap shear performance of synthesized Medhesives using a monofilament polyester mesh. N=6 for each sample.

Lap shear testing of the compounds was performed according to ASTM D5868. Briefly, Medhesive polymers solvent cast or heat-pressed onto a polyester mesh were cut into 1" by 2" segments with 1 cm area of adhesive overlap. The samples were activated by adding a known quantity of 1×PBS buffer to bovine pericardium substrate, and adhesive coated meshes were applied to the construct for a 20 min activation period. Samples were subsequently conditioned in PBS-soaked gauze for 1 hour at 37° C. After conditioning, samples were pull-tested at a rate of 10 mm/min until failure. Peak load and failure mode (adhesive/cohesive) were recorded and average peak stress was calculated and normalized to area of adhesive overlap. Medhesive-145 and Medhesive-179 performed well in lap shear testing (FIG. 19).

Example 26: Oxidant Synthesis

A requirement for compression molding of a thin film, and for spraying a polymer solution, is that the oxidant be in direct contact within the polymer at a large scale. While the oxidant may be solvent casted into the thin film at small scale (<2.5 g), scale up is desired. The oxidant is soluble in water, which activates the thin film, and weakly soluble in methanol, which contains some residual moisture. Conventionally, solvent casting is done by dissolving the oxidant in a dilute solution of methanol (≤7.5 mg/mL). This solution is then added to the polymer in chloroform. The solvent is subsequently evaporated in a hood to produce the thin film adhesive containing oxidant. However, as the process is scaled up, more methanol is required which increases the amount of moisture present. Additionally, as more solvent is required, longer evaporation times are needed. Scaling up the process past 2.5 g risks pre-activation of the polymer. Accordingly, it would be beneficial to use oxidants which are soluble in solvents that do not contain residual moisture (e.g., chloroform) which may help prevent pre-activation of the thin film during processing. Additionally, the oxidant would be required to be soluble in an aqueous environment so that when placed into contact with moist tissue it is released to activate the thin film.

Figure 20:
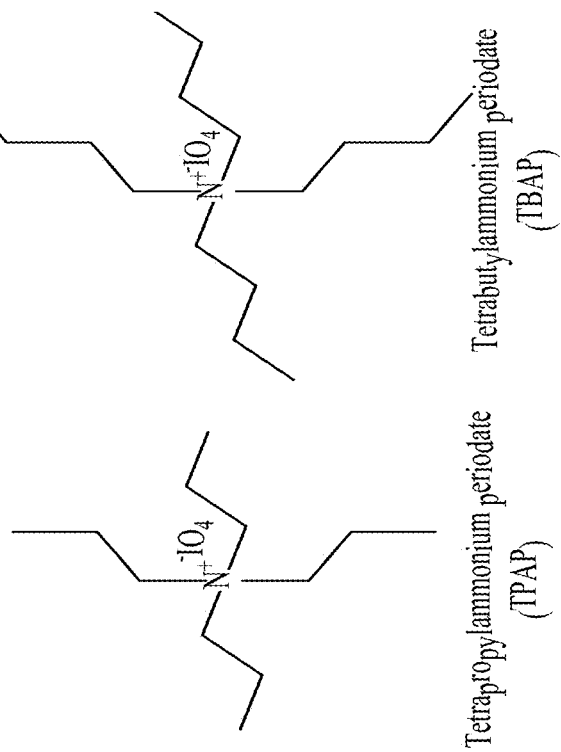
FIG. 20: Shows alkyl ammonium periodates as alternatives to sodium periodate.
Figure 21:
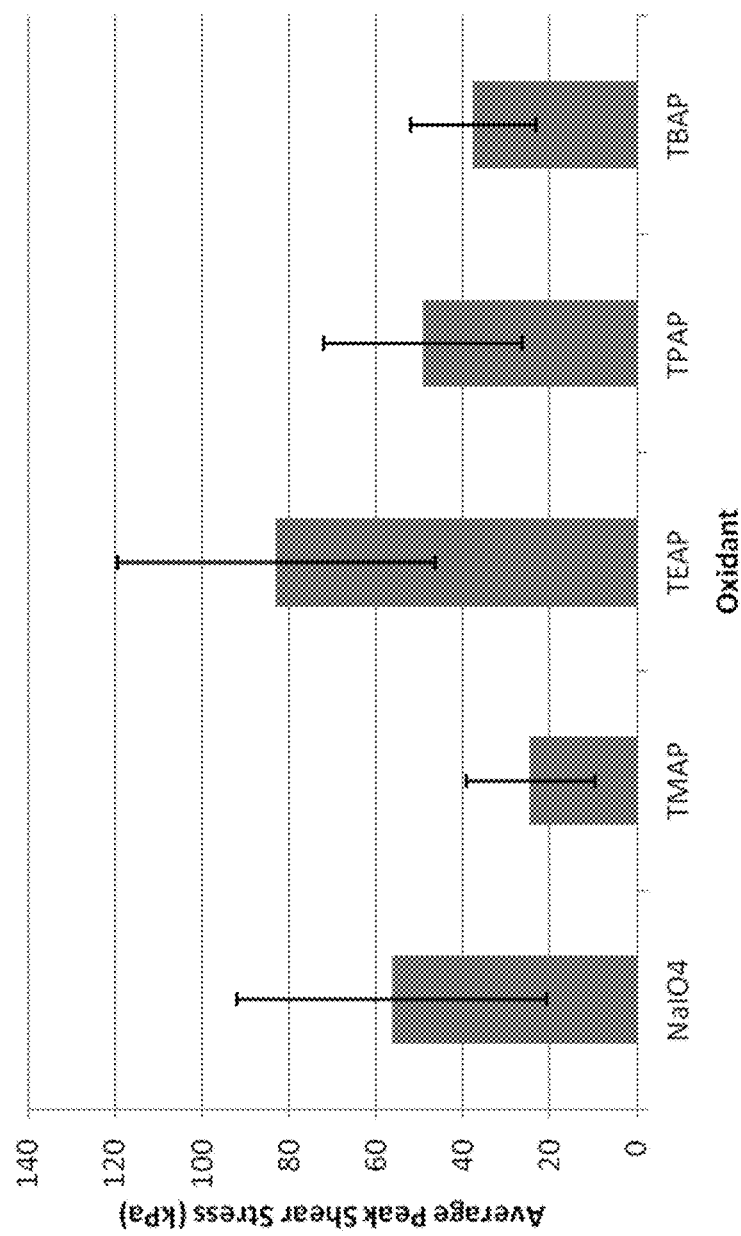
FIG. 21: Shows lap shear performance of newly synthesized oxidants using a monofilament polyester mesh with Medhesive-145. N=6 for each sample.
Figure 22:
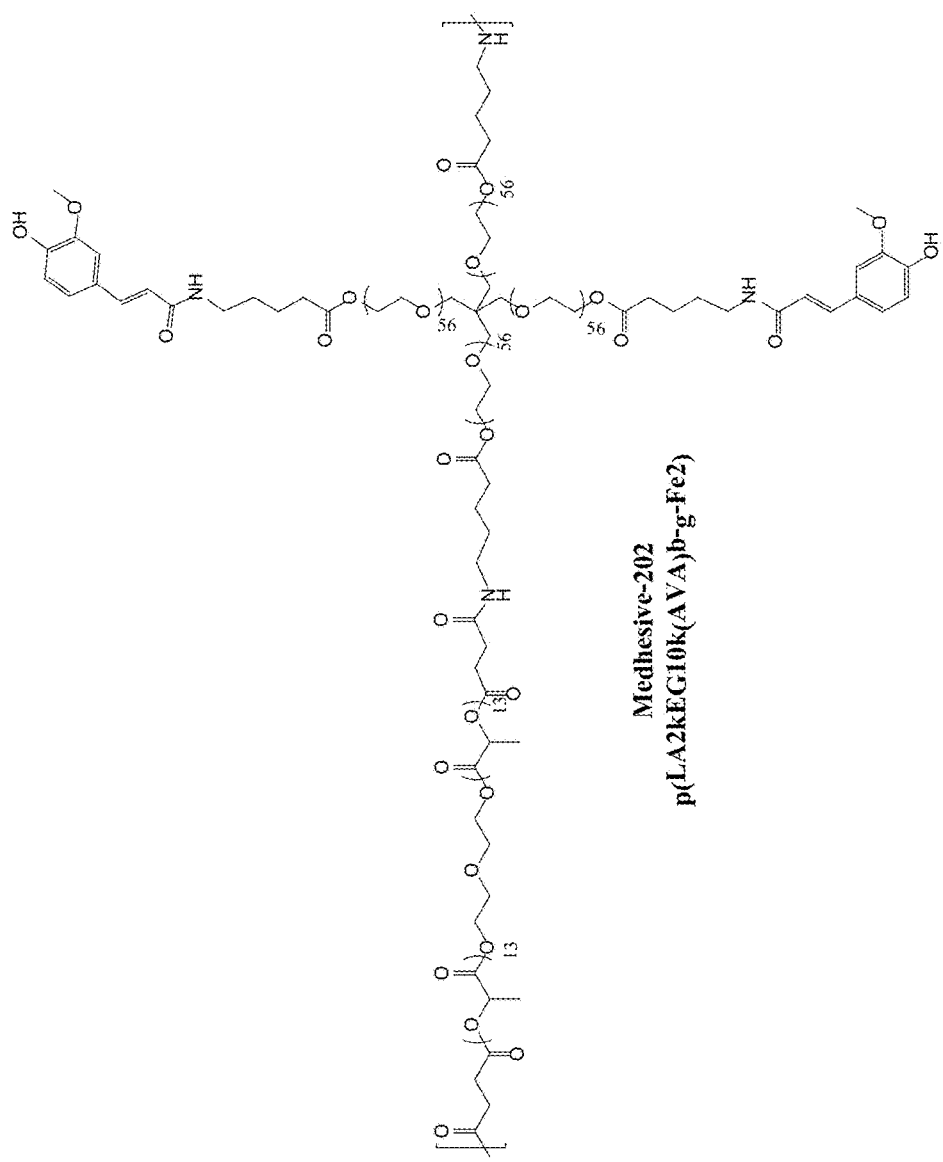
FIG. 22: Depicts general structure of Medhesive-202.

An effective and biocompatible oxidant is periodate. To make periodate more soluble in organic solvent, the counter-ion (sodium) was exchanged with an organic counter-ion. Counter-ions (TMAP, TEAP, TPAP and TBAP) are shown in FIG. 20. Lap shear testing was performed according to ASTM D5868 as described above. Both TPAP and TEAP are soluble in a wide variety of organic solvents (including chloroform) as well as in aqueous solutions (FIG. 21). TMAP showed lower than anticipated results, and is not soluble in many organic solvents. TBAP was soluble in many organic solvents but was not soluble in aqueous solutions.

Example 27: Synthesis of PLA2k-diSA 45 g of poly(L-lactide-co-D,L-lactide)-diol (PLA-diol prepared by known literature methods, 2,400 g/mol, 36 mmol) was dissolved in 160 mL Dichloromethane in a 500 mL round bottom flask while purging under nitrogen. Once completely dissolved, 11 g of succinic anhydride (108 mmol) was added followed by the addition of 15.3 mL of triethylamine (110 mmol). The reaction was allowed to react under nitrogen with stirring for ~24 hours. The solvent was removed via rotary evaporation and the redissolved in 600 mL of ethyl acetate. The solution was transferred to a separatory funnel. The mixture was extracted with two 100 mL portions of aqueous phosphoric acid (112 mmol), followed by three 100 mL portions of 10% w/w sodium chloride solution, and three 100 mL portions of nanopure water. The organic phase was collected and dried with anhydrous sodium sulfate. The dichloromethane solution was concentrated to a viscous oil and precipitated into 1500 mL of Heptane/IPA solvent mixture (70/30—w/w). The solid polymer was filtered and dried under vacuum for ~24 hours. The yield was 39.45 g. $^1$H NMR (400 MHz, CDCl$_3$/TMS): δ 4.8-5.3 (m, 37H, O—(OC—(CH$_3$)CH—O)9—CO—CH$_2$—CH$_2$—COOH), 4.19 (m, 4H, O—CH$_2$CH$_2$CH$_2$CH$_2$—O-PLA-), 2.68 (m, 8H, PLA—OOC—CH$_2$—CH$_2$—COOH), 1.68 (m, 4H, O—CH$_2$CH$_2$CH$_2$CH$_2$—O-PLA-), 1.3-1.6 (m, 111H, (OC—(CH$_3$)CH—O)9.

Example 28: Synthesis of Medhesive-202

7.47 g (6.23 mmol) of PLA2k-diSA, 33.3 g (12.7 mmol) of PEG10k-(AVA)$_4$, and 1.84 g (7.80 mmol) of Acetyl Ferulic Acid were dissolved in 250 mL DMF and 188 mL of chloroform. 5.917 g (15.60 mmol) of HBTU was dissolved in 250 mL of DMF. The HBTU solution was then added to the reaction mixture along with 3.01 mL (21.6 mmol) of triethylamine. The reaction was allowed to stir for 20 hours. 1.49 g (6.32 mmol) of Acetyl Ferulic Acid was added to the reaction followed by 0.654 mL (4.69 mmol) of triethylamine. The reaction was allowed to stir for another hour. The reaction was poured into 4 L of a heptane/IPA solvent mixture (90/10—w/w) and precipitated. The supernatant was decanted off and the polymer solid was washed with two 1 L portions of heptane-IPA (9/1), followed by two 1 L portions of hexane. The precipitate was removed and dried under vacuum for 6 hours. Once dry, the polymer was dissolved in 475 mL of chloroform and purged with nitrogen for 10 minutes. 98 mL of piperidine was added to the polymer solution. The reaction was allowed to proceed with stirring while purging with argon, for 40-45 minutes. The polymer was poured into 4 L of a heptane/IPA solvent mixture (70/30—w/w) and precipitated. The supernatant was decanted off and the polymer solid was washed with two 1 L portions of heptane-IPA (9/1), followed by two 1 L portions of hexane. The precipitate was vacuum filtered off and dried under vacuum. The polymer was purified by standard dialysis techniques and freeze dried. 36 g of material was obtained; IV=0.79+/−0.03 dl/g.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

What is claimed is:

1. A coating comprising
a) a compound comprising the formula (I)

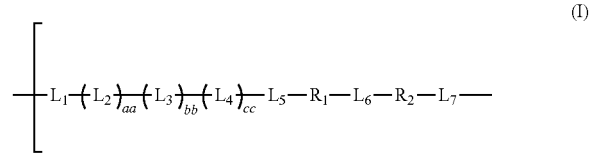

-continued

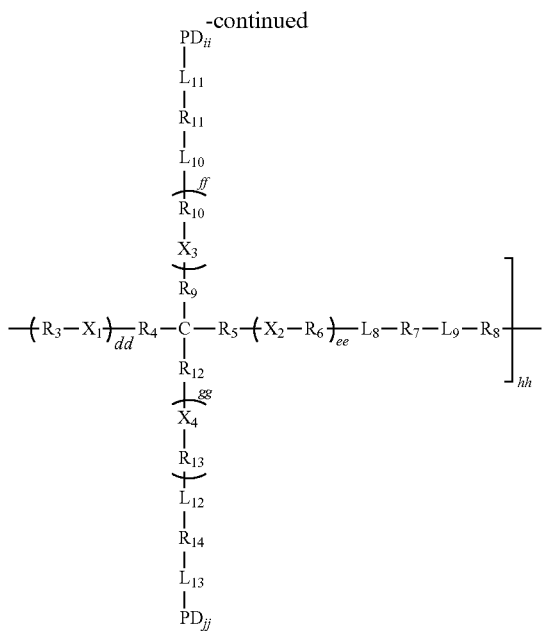

wherein
each $L_2$, $L_3$ and $L_4$ independently, is a linker;
each $L_1$, $L_5$, $L_6$, $L_7$, $L_8$, $L_9$, $L_{10}$, $L_{11}$ $L_{12}$ and $L_{13}$ independently, is a linker or a suitable linking group selected from amine, amide, ether, ester, urea carbonate or urethane linking groups;
each $X_1$, $X_2$, $X_3$ and $X_4$ independently, is an oxygen atom or NR;
R, if present, is H or a branched or unbranched C1-C10 alkyl group;
each $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ independently, is a branched or unbranched C1-C15 alkyl group;
each $PD_{ii}$ and $PD_{jj}$, independently, is a phenyl derivative residue selected from the group consisting of ferulic acid, isoferulic acid, sinapinic acid, syringic acid and vanillic acid;
aa is a value from 0 to about 80;
bb is a value from 0 to about 80;
cc is a value from 0 to about 80;
dd is a value from 1 to about 120;
ee is a value from 1 to about 120;
ff is a value from 1 to about 120;
gg is a value from 1 to about 120; and
hh is a value from 1 to about 80 and
b) an oxidant comprising tetraethylammonium periodate or tetrapropylammonium periodate.

2. The coating of claim 1, wherein $L_2$ is a residue of a C1-C15 alkyl lactone or lactam, a poly C1-C15 alkyl lactone or lactam, a polyester, or a compound comprising the formula $Y_4$—$R_{17}$—C(=O)—$Y_6$, wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

3. The coating of claim 2, wherein said alkyl lactone is a polycaprolactone.

4. The coating of claim 1, wherein $L_3$ is a residue of an alkylene diol, an alkylene diamine or a poly(alkylene oxide) polyether or derivative thereof.

5. The coating of claim 4, wherein $L_3$ is a poly(alkylene oxide) or —O—$CH_2CH_2$—O—$CH_2CH_2$—O—.

6. The coating of claim 1, wherein $L_2$ or $L_4$ is a residue of a C1-C15 alkyl lactone or lactam, a poly C1-C15 alkyl lactone or lactam, or a compound comprising the formula $Y_4$—$R_{17}$—C(=O)—$Y_6$, wherein $Y_4$ is OH, NHR, a halide, or an activated derivative of OH or NHR;
$R_{17}$ is a branched or unbranched C1-C15 alkyl group; and
$Y_6$ is NHR, a halide, or OR.

7. The coating of claim 6, wherein said alkyl lactone is polycaprolactone.

8. The coating of claim 1, wherein $X_1$, $X_2$, $X_3$ and $X_4$ are each O or NH.

9. The coating of claim 1, wherein $R_3$, $R_6$, $R_{10}$ and $R_{13}$ are each —$CH_2CH_2$—.

10. The coating of claim 1, wherein $X_1$, $X_2$, $X_3$ and $X_4$ are each O.

11. The coating of claim 1, wherein $R_4$, $R_5$, $R_9$ and $R_{12}$ are each —$CH_2$—.

12. The coating of claim 1, wherein $R_1$, $R_2$, $R_7$, $R_9$, $R_{11}$ and $R_{14}$ are a branched or unbranched alkane.

13. The coating of claim 12, wherein $R_1$, $R_2$, $R_7$, $R_9$, $R_{11}$ and $R_{14}$ are $CH_2$—$CH_2$— or —$CH_2$—$CH_2$—$CH_2$—.

14. The coating of claim 1, wherein $L_1$, $L_5$, $L_6$, $L_7$, $L_8$, $L_9$, $L_{19}$, $L_{11}$, $L_{12}$, and $L_{13}$ form an amide, ester or carbamate.

15. The coating of claim 1, wherein
$L_2$ is a residue of a polycaprolactone, a caprolactone, a polylactic acid, a polylactone or a lactic acid or lactone;
$L_3$ is a residue of polyethylene glycol;
$L_4$ is a residue of a polycaprolactone, a caprolactone, a polylactic acid, a polylactone or a lactic acid or lactone;
$X_1$, $X_2$, $X_3$ and $X_4$ are each O or NH;
$R_1$, $R_3$, $R_6$, $R_8$, $R_{10}$, and $R_{13}$ are each —$CH_2CH_2$—;
$R_4$, $R_5$, $R_9$ and $R_{12}$ are each —$CH_2$—;
$R_2$, $R_7$, $R_{11}$ and $R_{14}$ are each —$(CH2)_n$—, wherein n is 2, 3, or 4;
$L_1$, $L_5$, $L_7$, $L_8$, $L_{10}$, $L_{12}$ form an ester;
$L_6$, $L_9$, $L_{ii}$, and $L_{13}$ form an amide; and
$PD_{ii}$ and $PD_{jj}$ are residues selected from the group consisting of from ferulic acid (FA), isoferulic acid (IFA), syringic acid, and sinapinic acid (SAA).

16. The coating of claim 1, wherein
$L_2$ is a residue of a polycaprolactone, a caprolactone, a polylactic acid, a polylactone or a lactic acid or lactone;
$L_3$ is a residue of polyethylene glycol;
$L_4$ is a residue of a polycaprolactone, a caprolactone, a polylactic acid, a polylactone or a lactic acid or lactone;
$X_1$, $X_2$, $X_3$ and $X_4$ are each O or NH;
$R_3$, $R_6$, $R_{10}$, and $R_{13}$ are each —$CH_2CH_2$—;
$R_1$, $R_8$, $R_4$, $R_5$, $R_9$ and $R_{12}$ are each —$CH_2$—;
$R_2$, $R_7$, $R_{11}$ and $R_{14}$ are each —$(CH2)_n$—, wherein n is 2 or 3;
$L_1$, $L_5$, $L_7$, $L_8$, $L_{10}$, $L_{12}$ form an ester;
$L_6$, $L_9$, $L_{11}$, and $L_{13}$ form an amide; and
$PD_{ii}$ and $PD_{jj}$ are residues of ferulic acid or syringic acid.

17. A bioadhesive construct, comprising: a support suitable for tissue repair or reconstruction; and the coating of claim 1.

18. The bioadhesive construct of claim 17, wherein said oxidant is formulated with the coating.

19. The bioadhesive construct of claim 17, wherein said oxidant is applied to said coating.

20. The bioadhesive construct of claim 17, wherein said support is a film, a mesh, a membrane, a nonwoven or a prosthetic.

21. The bioadhesive construct of claim 17, comprising:
a) a support suitable for tissue repair or reconstruction;
b1) a first coating comprising a compound comprising the formula (I) and a polymer;

b2) a second coating coated onto said first coating, wherein said second coating comprises a compound comprising the formula (I); and
c) an oxidant comprising tetraethylammonium periodate or tetrapropylammonium periodate.

22. The bioadhesive construct of claim 17, comprising:
a) a support suitable for tissue repair or reconstruction;
b1) a first coating comprising a compound comprising the formula (I) and a first polymer;
b2) a second coating coated onto said first coating, wherein said second coating comprises a second compound comprising the formula (I) and a second polymer, wherein said first and second polymer may be the same or different, and wherein said first and said second compound comprising the formula (I) can be the same or different; and
c) an oxidant comprising tetraethylammonium periodate or tetrapropylammonium periodate.

23. The bioadhesive construct of claim 17 comprising:
a) a support suitable for tissue repair or reconstruction;
b1) a first coating comprising a first compound comprising the formula (I);
b2) a second coating coated onto said first coating, wherein said second compound comprising the formula (I), wherein said first and second compound comprising the formula (I) can be the same or different; and
c) an oxidant comprising tetraethylammonium periodate or tetrapropylammonium periodate.

24. A bioadhesive construct comprising:
a support suitable for tissue repair or reconstruction; and
the coating of claim 1, wherein the coating comprises a blend of a polymer and a compound comprising formula (I).

25. The bioadhesive construct of claim 24, wherein the polymer is present in a range of about 1 to 50 percent by weight.

26. The bioadhesive construct of claim 25, wherein said polymer is present is present at an amount of about 30 percent by weight.

27. The bioadhesive construct of claim 25, wherein said oxidant is applied to said coating.

28. The coating of claim 1, wherein said oxidant is formulated with the coating.

29. The coating of claim 1, wherein said oxidant is applied to said coating.

* * * * *